United States Patent
Chernoff et al.

(10) Patent No.: US 11,240,996 B2
(45) Date of Patent: Feb. 8, 2022

(54) MICE WITH TRANSGENE OF IBOX PEPTIDE INHIBITOR OF GROUP B P21-ACTIVATED KINASES

(71) Applicant: Institute For Cancer Research, Philadelphia, PA (US)

(72) Inventors: Jonathan Chernoff, Philadelphia, PA (US); Hoi Yee Chow, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 15/683,948

(22) Filed: Aug. 23, 2017

(65) Prior Publication Data

US 2018/0055020 A1 Mar. 1, 2018

Related U.S. Application Data

(60) Provisional application No. 62/378,769, filed on Aug. 24, 2016.

(51) Int. Cl.
| | |
|---|---|
| *A01K 67/027* | (2006.01) |
| *C12N 15/00* | (2006.01) |
| *C07K 14/47* | (2006.01) |
| *C12N 9/10* | (2006.01) |
| *C12N 9/14* | (2006.01) |

(52) U.S. Cl.
CPC ...... *A01K 67/0275* (2013.01); *A01K 67/0278* (2013.01); *C07K 14/4703* (2013.01); *C12N 9/1088* (2013.01); *C12N 9/14* (2013.01); *C12Y 205/01018* (2013.01); *C12Y 306/05002* (2013.01); *A01K 2217/052* (2013.01); *A01K 2227/105* (2013.01); *A01K 2267/0331* (2013.01); *C07K 2319/00* (2013.01)

(58) Field of Classification Search
CPC ................ A01K 67/0275; C07K 14/4703
USPC .................................... 800/18, 21
See application file for complete search history.

(56) References Cited

U.S. PATENT DOCUMENTS

2017/0335342 A1* 11/2017 Chernoff ............ C12N 15/8509

OTHER PUBLICATIONS

Nyabi (Nucleic Acid Res., 2009, vol. 37, No. 7, e55; Supplementary Fig. 1).*
Baskaran (Nature Comm., Nov. 26, 2015, vol. 6, No. 8681, p. 1-11).*
Magnuson (Cell Metab., 2013, vol. 18, p. 9-20).*
Chen (Cancer Biol. Therapy, Nov. 2008, vol. 7. No. 11, p. 1793-1802).*
Azmi (J. Clin. Oncology, 2014, vol. 32, No. 3, Suppl., p. 233).*
Hingorani (Cancer Cell, 2003, vol. 4, p. 437-450).*

* cited by examiner

*Primary Examiner* — Michael C Wilson
(74) *Attorney, Agent, or Firm* — Stadley Ronon Stevens & Young, LLP

(57) ABSTRACT

Mice comprising a transgene encoding a peptide (iBox) inhibitor of Group B p21-activated kinase are provided. Also provided are cells, tissue, and organs obtained from such transgenic mice. Also provided are methods for producing mice comprising an iBox-encoding transgene.

9 Claims, 30 Drawing Sheets

Specification includes a Sequence Listing.

Figure 2

```
        PacI
5'      taagggatctgtagggcgcagtagtccagggtttccttgatgatgtcatacttatcctgtccctt
...     ++++++++++++++++++++++++++++++++++++++++++++++++++++++++++++++++++  65
3'      attccctagacatcccgcgtcatcaggtcccaaaggaactactacagtatgaataggacagggaa ttttttccacagctcgcggttgaggacaaactcttcgcggtctttccagtggggatcgacggtat
        ++++++++++++++++++++++++++++++++++++++++++++++++++++++++++++++++++  130
        aaaaaaggtgtcgagcgccaactcctgtttgagaagcgccagaaaggtcacccctagctgccata cgtagagtcgaggccgctctagaactagtggatccggaacccttaatataacttcgtataatgta
        ++++++++++++++++++++++++++++++++++++++++++++++++++++++++++++++++++  195
        gcatctcagctccggcgagatcttgatcacctaggccttgggaattatattgaagcatattacat
                                SK primer →              ← loxP tgctatacgaagttattaggtccctcgacctgcaggaattctaccgggtaggggaggcgcttttc
        ++++++++++++++++++++++++++++++++++++++++++++++++++++++++++++++++++  260
        acgatatgcttcaataatccagggagctggacgtccttaagatggcccatcccctccgcgaaaag
     ← loxP                                      [ PGK promoter → ccaaggcagtctggagcatgcgctttagcagcccgctggcacttggcgctacacaagtggcctc
        ++++++++++++++++++++++++++++++++++++++++++++++++++++++++++++++++++  325
        ggttccgtcagacctcgtacgcgaaatcgtcgggcgaccgtgaaccgcgatgtgttcaccggag
                                    PGK promoter                      →

AgeI
        tggcctcgcacacattccacatccaccggtagcgccaaccggctccgttctttggtggcccttc
        ++++++++++++++++++++++++++++++++++++++++++++++++++++++++++++++++++  390
        accggagcgtgtgtaaggtgtaggtggccatcgcggttggccgaggcaagaaaccaccggggaag
                                    PGK promoter                      → gcgccaccttctactcctcccctagtcaggaagttccccccgccccgcagctcgcgtcgtgcag
        ++++++++++++++++++++++++++++++++++++++++++++++++++++++++++++++++++  455
        cgcggtggaagatgaggaggggatcagtccttcaagggggggcggggcgtcgagcgcagcacgtc
                                    PGK promoter                      → gacgtgacaaatggaagtagcacgtctcactagtctcgtgcagatggacagcaccgctgagcaat
        ++++++++++++++++++++++++++++++++++++++++++++++++++++++++++++++++++  520
        ctgcactgtttaccttcatcgtgcagagtgatcagagcacgtctacctgtcgtggcgactcgtta
                                    PGK promoter                      → ggaagcgggtaggcctttggggcagcggccaatagcagctttgctccttcgctttctgggctcag
        ++++++++++++++++++++++++++++++++++++++++++++++++++++++++++++++++++  585
        ccttcgcccatccggaaacccgtcgccggttatcgtcgaaacgaggaagcgaaagacccgagtc
                                    PGK promoter                      → aggctgggaaggggtgggtccggggcgggctcaggggcgggctcaggggcggggcgggcgcgaa
        ++++++++++++++++++++++++++++++++++++++++++++++++++++++++++++++++++  650
        tccgacccttccccacccaggccccgcccgagtccccgcccgagtccccgccccgcccgcgctt
                                    PGK promoter                      →
```

Figure 2 (cont.)

```
ggtcctcccgaggcccggcattctcgcacgcttcaaaagcgcacgtctgccgcgctgttctcctc
++++|++++|++++|++++|++++|++++|++++|++++|++++|++++|++++|++++|++++|     715
ccaggagggctccgggccgtaagagcgtgcgaagttttcgcgtgcagacggcgcgacaagaggag
        ─────────────────────────────────────────────────────────>
                            PGK promoter ttcctcatctccgggcctttcgacctgcagccaatatgggatcggccattgaacaagatggattg
++++|++++|++++|++++|++++|++++|++++|++++|++++|++++|++++|++++|++++|     780
aaggagtagaggcccggaaagctggacgtcggttatacccta gccggtaacttgttctacctaac
                                          1         5           10
                                          M  G  S  A  I  E  Q  D  G  L
 ───────────────────────>                 ┌──────────────────────────
       PGK promoter                                    NeoR/KanR     > cacgcaggttctccggccgcttgggtggagaggctattcggctatgactgggcacaacagacaat
++++|++++|++++|++++|++++|++++|++++|++++|++++|++++|++++|++++|++++|     845
gtgcgtccaagaggccggcgaacccacctctccgataagccgatactgacccgtgttgtctgtta
         15            20            25            30
  H  A  G  S  P  A  A  W  V  E  R  L  F  G  Y  D  W  A  Q  Q  T  I
────────────────────────────────────────────────────────────────────>
                              NeoR/KanR cggctgctctgatgccgccgtgttccggctgtcagcgcaggggcgcccggttcttttttgtcaaga
++++|++++|++++|++++|++++|++++|++++|++++|++++|++++|++++|++++|++++|     910
gccgacgagactacggcggcacaaggccgacagtcgcgtccccgcgggccaagaaaaacagttct
         35            40            45            50
  G  C  S  D  A  A  V  F  R  L  S  A  Q  G  R  P  V  L  F  V  K
────────────────────────────────────────────────────────────────────>
                              NeoR/KanR ccgacctgtccggtgccctgaatgaactgcaggacgaggcagcgcggctatcgtggctggccacg
++++|++++|++++|++++|++++|++++|++++|++++|++++|++++|++++|++++|++++|     975
ggctggacaggccacgggacttacttgacgtcctgctccgtcgcgccgatagcaccgaccggtgc
         55            60            65            70            75
  T  D  L  S  G  A  L  N  E  L  Q  D  E  A  A  R  L  S  W  L  A  T
────────────────────────────────────────────────────────────────────>
                              NeoR/KanR PflFI
                  Tth111I
                  |
acgggcgttccttgcgcagctgtgctcgacgttgtcactgaagcgggaagggactggctgctatt
++++|++++|++++|++++|++++|++++|++++|++++|++++|++++|++++|++++|++++|    1040
tgcccgcaaggaacgcgtcgacacgagctgcaacagtgacttcgcccttccctgaccgacgataa
         80            85            90            95
  T  G  V  P  C  A  A  V  L  D  V  V  T  E  A  G  R  D  W  L  L  L
────────────────────────────────────────────────────────────────────>
                              NeoR/KanR gggcgaagtgccggggcaggatctcctgtcatctcaccttgctcctgccgagaaagtatccatca
++++|++++|++++|++++|++++|++++|++++|++++|++++|++++|++++|++++|++++|    1105
cccgcttcacggccccgtcctagaggacagtagagtggaacgaggacggctctttcataggtagt
        100           105           110           115
  G  E  V  P  G  Q  D  L  L  S  S  H  L  A  P  A  E  K  V  S  I
────────────────────────────────────────────────────────────────────>
                              NeoR/KanR
```

Figure 2 (cont.)

```
          tggctgatgcaatgcggcggctgcatacgcttgatccggctacctgcccattcgaccaccaagcg
          ++++++++++++++++++++++++++++++++++++++++++++++++++++++++++++++++++     1170
          accgactacgttacgccgccgacgtatgcgaactaggccgatggacgggtaagctggtggttcgc
              120         125         130         135         140
           M  A  D  A  M  R  R  L  H  T  L  D  P  A  T  C  P  F  D  H  Q  A
           ─────────────────────── NeoR/KanR ─────────────────────────────>

BsaAI
                           |
          aaacatcgcatcgagcgagcacgtactcggatggaagccggtcttgtcgatcaggatgatctgga
          ++++++++++++++++++++++++++++++++++++++++++++++++++++++++++++++++++     1235
          tttgtagcgtagctcgctcgtgcatgagcctaccttcggccagaacagctagtcctactagacct
              145         150         155         160
           K  H  R  I  E  R  A  R  T  R  M  E  A  G  L  V  D  Q  D  D  L  D
           ─────────────────────── NeoR/KanR ─────────────────────────────> cgaagagcatcaggggctcgcgccagccgaactgttcgccaggctcaaggcgcgcatgcccgacg
          ++++++++++++++++++++++++++++++++++++++++++++++++++++++++++++++++++     1300
          gcttctcgtagtccccgagcgcggtcggcttgacaagcggtccgagttccgcgcgtacgggctgc
              165         170         175         180
           E  E  H  Q  G  L  A  P  A  E  L  F  A  R  L  K  A  R  M  P  D
           ─────────────────────── NeoR/KanR ─────────────────────────────> gcgatgatctcgtcgtgacccatggcgatgcctgcttgccgaatatcatggtggaaaatggccgc
          ++++++++++++++++++++++++++++++++++++++++++++++++++++++++++++++++++     1365
          cgctactagagcagcactgggtaccgctacggacgaacggcttatagtaccacctttaccggcg
              185         190         195         200         205
           G  D  D  L  V  V  T  H  G  D  A  C  L  P  N  I  M  V  E  N  G  R
           ─────────────────────── NeoR/KanR ─────────────────────────────>

RsrII
                                        |
          ttttctggattcatcgactgtggccggctgggtgtggcggaccgctatcaggacatagcgttggc
          ++++++++++++++++++++++++++++++++++++++++++++++++++++++++++++++++++     1430
          aaaagacctaagtagctgacaccggccgacccacaccgcctggcgatagtcctgtatcgcaaccg
              210         215         220         225
           F  S  G  F  I  D  C  G  R  L  G  V  A  D  R  Y  Q  D  I  A  L  A
           ─────────────────────── NeoR/KanR ─────────────────────────────> tacccgtgatattgctgaagagcttggcggcgaatgggctgaccgcttcctcgtgctttacggta
          ++++++++++++++++++++++++++++++++++++++++++++++++++++++++++++++++++     1495
          atgggcactataacgacttctcgaaccgccgcttacccgactggcgaaggagcacgaaatgccat
              230         235         240         245
           T  R  D  I  A  E  E  L  G  G  E  W  A  D  R  F  L  V  L  Y  G
           ─────────────────────── NeoR/KanR ─────────────────────────────> tcgccgctcccgattcgcagcgcatcgccttctatcgccttcttgacgagttcttctgaggggat
          ++++++++++++++++++++++++++++++++++++++++++++++++++++++++++++++++++     1560
          agcggcgagggctaagcgtcgcgtagcggaagatagcggaagaactgctcaagaagactcccta
              250         255         260         265
           I  A  A  P  D  S  Q  R  I  A  F  Y  R  L  L  D  E  F  F  *
           ─────────────────────── NeoR/KanR ─────────────────────────────> ccgctgtaagtctgcagaaattgatgatctattaaacaataaagatgtccactaaaatggaagtt
          ++++++++++++++++++++++++++++++++++++++++++++++++++++++++++++++++++     1625
          ggcgacattcagacgtctttaactactagataatttgttatttctacaggtgattttaccttcaa
```

Figure 2 (cont.)

```
tttcctgtcatactttgttaagaagggtgagaacagagtacctacattttgaatggaaggattgg
aaaggacagtatgaaacaattcttcccactcttgtctcatggatgtaaaacttaccttcctaacc    1690 agctacggggtggggtgggtgggattagataaatgcctgctcttactgaaggctcttact
tcgatgccccacccccaccccacctaatctatttacggacgagaaatgacttcgagaaatga    1755 attgctttatgataatgtttcatagttggatatcataatttaaacaagcaaaaccaaattaaggg
taacgaaatactattacaaagtatcaacctatagtattaaatttgttcgttttggtttaattccc    1820 ccagctcattcctcccactcatgatctatagatctatagatctctcgtgggatcattgtttttct
ggtcgagtaaggagggtgagtactagatatctagatatctagagagcacctagtaacaaaaaga    1885 cttgattcccactttgtggttctaagtactgtggtttccaaatgtgtcagtttcatagcctgaag
gaactaagggtgaaacaccaagattcatgacaccaaaggtttacacagtcaaagtatcggacttc    1950 aacgagatcagcagcctctgttccacatacacttcattctcagtattgttttgccaagttctaat
ttgctctagtcgtcggagacaaggtgtatgtgaagtaagagtcataacaaaacggttcaagatta    2015 tccatcagaagcttgcagatctgcgactctagaggatctgcgactctagaggatcataatcagcc
aggtagtcttcgaacgtctagacgctgagatctcctagacgctgagatctcctagtattagtcgg    2080 ataccacatttgtagaggttttacttgctttaaaaaacctcccacacctcccctgaacctgaaa
tatggtgtaaacatctccaaaatgaacgaaattttttggagggtgtggagggggacttggacttt    2145 cataaaatgaatgcaattgttgttgttaacttgtttattgcagcttataatggttacaaataaag
gtattttacttacgttaacaacaacaattgaacaaataacgtcgaatattaccaatgtttatttc    2210
```
`SV40 poly(A) signal`

```
caatagcatcacaaatttcacaaataaagcatttttttcactgcattctagttgtggtttgtcca
gttatcgtagtgtttaaagtgtttatttcgtaaaaaaagtgacgtaagatcaacaccaaacaggt    2275
```
`SV40 poly(A) signal`

```
aactcatcaatgtatcttatcatgtctggatctgcgactctagaggatcataatcagccatacca
ttgagtagttacatagaatagtacagacctagacgctgagatctcctagtattagtcggtatggt    2340
```
`SV40 poly(A) signal`

```
catttgtagaggttttacttgctttaaaaaacctcccacacctcccctgaacctgaaacataaa
gtaaacatctccaaaatgaacgaaattttttggagggtgtggagggggacttggactttgtattt    2405
```

Figure 2 (cont.)

```
     atgaatgcaattgttgttgttaacttgtttattgcagcttataatggttacaaataaagcaatag
     ++++++++++++++++++++++++++++++++++++++++++++++++++++++++++++++++++    2470
     tacttacgttaacaacaacaattgaacaaataacgtcgaatattaccaatgtttatttcgttatc
                             SV40 poly(A) signal catcacaaatttcacaaataaagcattttttcactgcattctagttgtggtttgtccaaactca
     ++++++++++++++++++++++++++++++++++++++++++++++++++++++++++++++++++    2535
     gtagtgtttaaagtgtttatttcgtaaaaaagtgacgtaagatcaacaccaaacaggtttgagt
                             SV40 poly(A) signal tcaatgtatcttatcatgtctggatctgcgactctagaggatcataatcagccataccacatttg
     ++++++++++++++++++++++++++++++++++++++++++++++++++++++++++++++++++    2600
     agttacatagaatagtacagacctagacgctgagatctcctagtattagtcggtatggtgtaaac
        SV40 poly(A) signal tagaggttttacttgctttaaaaaacctcccacacctcccccctgaacctgaaacataaaatgaat
     ++++++++++++++++++++++++++++++++++++++++++++++++++++++++++++++++++    2665
     atctccaaaatgaacgaaatttttggagggtgtggaggggggacttggactttgtatttactta gcaattgttgttgttaacttgtttattgcagcttataatggttacaaataaagcaatagcatcac
     ++++++++++++++++++++++++++++++++++++++++++++++++++++++++++++++++++    2730
     cgttaacaacaacaattgaacaaataacgtcgaatattaccaatgtttatttcgttatcgtagtg
                             SV40 poly(A) signal aaatttcacaaataaagcattttttcactgcattctagttgtggtttgtccaaactcatcaatg
     ++++++++++++++++++++++++++++++++++++++++++++++++++++++++++++++++++    2795
     tttaaagtgtttatttcgtaaaaaagtgacgtaagatcaacaccaaacaggtttgagtagttac
                             SV40 poly(A) signal tatcttatcatgtctggatccccatcaagctgatccggaacccttaatataacttcgtataatgt
     ++++++++++++++++++++++++++++++++++++++++++++++++++++++++++++++++++    2860
     atagaatagtacagacctagggggtagttcgactaggccttgggaattatattgaagcatattaca
       SV40 poly(A) signal                                        loxP NheI    BmtI
     atgctatacgaagttattaggtccctcgacctgcagcccaagctagcttatcgataccgtcgacc
     ++++++++++++++++++++++++++++++++++++++++++++++++++++++++++++++++++    2925
     tacgatatgcttcaataatccagggagctggacgtcgggttcgatcgaatagctatggcagctgg
   <   loxP                                                KS primer NotI
     tcgaatcacaagtttGTACAAAAAAGCAGGCTCCGCGGCCGCCCCCTTCACCATGTCCCCTATAC
     ++++++++++++++++++++++++++++++++++++++++++++++++++++++++++++++++++    2990
     agcttagtgttcaaaCATGTTTTTTCGTCCGAGGCGCCGGCGGGGGAAGTGGTACAGGGGATATG
                                                            1
                                                        M  S  P  I
   <                      attB1                            GST       >
    KS primer
```

Figure 2 (cont.)

```
TAGGTTATTGGAAAATTAAGGGCCTTGTGCAACCCACTCGACTTCTTTTGGAATATCTTGAAGAA
ATCCAATAACCTTTTAATTCCCGGAACACGTTGGGTGAGCTGAAGAAAACCTTATAGAACTTCTT
 5         10        15        20        25
 L  G  Y  W  K  I  K  G  L  V  Q  P  T  R  L  L  E  Y  L  E  E
                              GST
```
3055

```
AAATATGAAGAGCATTTGTATGAGCGCGATGAAGGTGATAAATGGCGAAACAAAAAGTTTGAATT
TTTATACTTCTCGTAAACATACTCGCGCTACTTCCACTATTTACCGCTTTGTTTTTCAAACTTAA
     30            35            40           45
  K  Y  E  E  H  L  Y  E  R  D  E  G  D  K  W  R  N  K  K  F  E  L
                              GST
```
3120

```
GGGTTTGGAGTTTCCCAATCTTCCTTATTATATTGATGGTGATGTTAAATTAACACAGTCTATGG
CCCAAACCTCAAAGGGTTAGAAGGAATAATATAACTACCACTACAATTTAATTGTGTCAGATACC
     50           55           60           65
  G  L  E  F  P  N  L  P  Y  Y  I  D  G  D  V  K  L  T  Q  S  M
                              GST
```
3185

```
CCATCATACGTTATATAGCTGACAAGCACAACATGTTGGGTGGTTGTCCAAAAGAGCGTGCAGAG
GGTAGTATGCAATATATCGACTGTTCGTGTTGTACAACCCACCAACAGGTTTTCTCGCACGTCTC
  70          75           80           85          90
  A  I  I  R  Y  I  A  D  K  H  N  M  L  G  G  C  P  K  E  R  A  E
                              GST
```
3250

```
ATTTCAATGCTTGAAGGAGCGGTTTTGGATATTAGATACGGTGTTTCGAGAATTGCATATAGTAA
TAAAGTTACGAACTTCCTCGCCAAAACCTATAATCTATGCCACAAAGCTCTTAACGTATATCATT
       95          100          105         110
  I  S  M  L  E  G  A  V  L  D  I  R  Y  G  V  S  R  I  A  Y  S  K
                              GST
```
3315

```
                                                         BstBI
AGACTTTGAAACTCTCAAAGTTGATTTTCTTAGCAAGCTACCTGAAATGCTGAAAATGTTCGAAG
TCTGAAACTTTGAGAGTTTCAACTAAAAGAATCGTTCGATGGACTTTACGACTTTTACAAGCTTC
      115         120           125          130
  D  F  E  T  L  K  V  D  F  L  S  K  L  P  E  M  L  K  M  F  E
                              GST
```
3380

```
              SwaI
ATCGTTTATGTCATAAAACATATTTAAATGGTGATCATGTAACCCATCCTGACTTCATGTTGTAT
TAGCAAATACAGTATTTTGTATAAATTTACCACTAGTACATTGGGTAGGACTGAAGTACAACATA
 135         140           145          150          155
  D  R  L  C  H  K  T  Y  L  N  G  D  H  V  T  H  P  D  F  M  L  Y
                              GST
```
3445

Figure 2 (cont.)

```
GACGCTCTTGATGTTGTTTTATACATGGACCCAATGTGCCTGGATGCGTTCCCAAAATTAGTTTG
++++|++++|++++|++++|++++|++++|++++|++++|++++|++++|++++|++++|++++|    3510
CTGCGAGAACTACAACAAAATATGTACCTGGGTTACACGGACCTACGCAAGGGTTTTAATCAAAC
........160.........165.........170.........175........
    D  A  L  D  V  V  L  Y  M  D  P  M  C  L  D  A  F  P  K  L  V  C
    ▓▓▓▓▓▓▓▓▓▓▓▓▓▓▓▓▓▓▓▓▓▓▓▓ GST ▓▓▓▓▓▓▓▓▓▓▓▓▓▓▓▓▓▓▓▓▓▓▓▓ >

TTTTAAAAAACGTATTGAAGCTATCCCACAAATTGATAAGTACTTGAAATCCAGCAAGTATATAG
++++|++++|++++|++++|++++|++++|++++|++++|++++|++++|++++|++++|++++|    3575
AAAATTTTTTGCATAACTTCGATAGGGTGTTTAACTATTCATGAACTTTAGGTCGTTCATATATC
........180.........185.........190.........195........
    F  K  K  R  I  E  A  I  P  Q  I  D  K  Y  L  K  S  S  K  Y  I
    ▓▓▓▓▓▓▓▓▓▓▓▓▓▓▓▓▓▓▓▓▓▓▓▓ GST ▓▓▓▓▓▓▓▓▓▓▓▓▓▓▓▓▓▓▓▓▓▓▓▓ > pGEX 5' Sequencing Primer
              [GGGCTGGCAAGCCACGTTTGGTG]
CATGGCCTTTGCAGGGCTGGCAAGCCACGTTTGGTGGTGGCGACCATCCTCCAAAATCGGATCTG
++++|++++|++++|++++|++++|++++|++++|++++|++++|++++|++++|++++|++++|    3640
GTACCGGAAACGTCCCGACCGTTCGGTGCAAACCACCACCGCTGGTAGGAGGTTTTAGCCTAGAC
.200........205.........210.........215.........1...
  A  W  P  L  Q  G  W  Q  A  T  F  G  G  G  D  H  P  P  K  S  D  L
  ▓▓▓▓▓▓▓▓▓▓▓▓▓▓▓▓▓▓▓▓ GST ▓▓▓▓▓▓▓▓▓▓▓▓▓▓▓▓▓▓▓▓ >---->  ▓▓▓▓ >
                                                        thrombin site GTTCCGCGTGGATCCgaagcagaggactggacggcagccctgctgaacaggggccgcagtcggca
++++|++++|++++|++++|++++|++++|++++|++++|++++|++++|++++|++++|++++|    3705
CAAGGCGCACCTAGGcttcgtctcctgacctgccgtcgggacgacttgtccccggcgtcagccgt
          ..5........
  V  P  R  G  S  E  A  E  D  W  T  A  A  L  L  N  R  G  R  S  R  Q
  ▓ thrombin site ▓ >------ (in frame with thrombin site) --------▶
                    ▓▓▓▓▓▓▓▓▓▓▓▓▓▓▓▓▓▓▓▓ IBox ▓▓▓▓▓▓▓▓▓▓▓▓▓▓▓▓▓▓▓▓ > gccccTggtgctaggggataactgttttgctgatttagttcacaattggatggagttgcctgaat
++++|++++|++++|++++|++++|++++|++++|++++|++++|++++|++++|++++|++++|    3770
cggggaccacgatcccctattgacaaaacgactaaatcaagtgttaacctacctcaacggactta
    P  L  V  L  G  D  N  C  F  A  D  L  V  H  N  W  M  E  L  P  E
    ------------- (in frame with thrombin site) ---------------▶
    ▓▓▓▓▓▓▓▓▓▓▓▓▓▓▓▓▓▓▓▓▓▓▓▓ IBox ▓▓▓▓▓▓▓▓▓▓▓▓▓▓▓▓▓▓▓▓▓▓▓▓ >

AscI
                     |
gaGAATTCGCCAAGGGTGGGCGCGCCGACCCAGCTTTcttgtacaaagtggtgattcgaggtcga
++++|++++|++++|++++|++++|++++|++++|++++|++++|++++|++++|++++|++++|    3835
ctCTTAAGCGGTTCCCACCCGCGCGGCTGGGTCGAAAgaacatgtttcaccactaagctccagct
▓
-▶                       ◀▓▓▓▓ attB2 ▓▓▓▓▶    ▓ KS primer ▓ >
▓
IBox
```

Figure 2 (cont.)

```
cggtatcgataagcttgatatcgaattccgccccccccctctccctccccccccctaacgtta
++++|++++|++++|++++|++++|++++|++++|++++|++++|++++|++++|++++|++++|    3900
gccatagctattcgaactatagcttaaggcgggggggggagagggagggggggggattgcaat
◄ KS primer ctggccgaagccgcttggaataaggccggtgtgcgtttgtctatatgttattttccaccatattg
++++|++++|++++|++++|++++|++++|++++|++++|++++|++++|++++|++++|++++|    3965
gaccggcttcggcgaaccttattccggccacacgcaaacagatatacaataaaaggtggtataac AvrII
                                                              |
ccgtcttttggcaatgtgagggcccggaaacctggccctgtcttcttgacgagcattcctagggg
++++|++++|++++|++++|++++|++++|++++|++++|++++|++++|++++|++++|++++|    4030
ggcagaaaaccgttacactcccgggcctttggaccgggacagaagaactgctcgtaaggatcccc tctttccctctcgccaaaggaatgcaaggtctgttgaatgtcgtgaaggaagcagttcctctgg
++++|++++|++++|++++|++++|++++|++++|++++|++++|++++|++++|++++|++++|    4095
agaaaggggagagcggtttccttacgttccagacaacttacagcacttccttcgtcaaggagacc aagcttcttgaagacaaacaacgtctgtagcgacccttttgcaggcagcggaaccccccacctggc
++++|++++|++++|++++|++++|++++|++++|++++|++++|++++|++++|++++|++++|    4160
ttcgaagaacttctgtttgttgcagacatcgctgggaaacgtccgtcgccttgggggtggaccg gacatggatagttgtggaagagtcaaatggctctcctcaagcgtattcaacaagggctgaagg
++++|++++|++++|++++|++++|++++|++++|++++|++++|++++|++++|++++|++++|    4225
ctgtacctatcaacacctttctcagtttaccgagaggagttcgcataagttgttccccgacttcc Acc65I    KpnI
          |       |
atgcccagaaggtacccattgtatgggatctgatctggggcctcggtgcacatgctttacatgt
++++|++++|++++|++++|++++|++++|++++|++++|++++|++++|++++|++++|++++|    4290
tacgggtcttccatggggtaacatacctagactagaccccggagccacgtgtacgaaatgtaca gtttagtcgaggttaaaaaacgtctaggccccccgaaccacggggacgtggttttggtttgaaaa
++++|++++|++++|++++|++++|++++|++++|++++|++++|++++|++++|++++|++++|    4355
caaatcagctccaattttttgcagatccggggggcttggtgccctgcaccaaaccaaactttt acacgatgataatatggccacaaccatggtgagcaagggcgaggagctgttcaccggggtggtgc
++++|++++|++++|++++|++++|++++|++++|++++|++++|++++|++++|++++|++++|    4420
tgtgctactattataccggtgttggtaccactcgttcccgctcctcgacaagtggccccaccacg
                                 1           5              10
                                 M V S K G E E L F T G V V
                                     ▓1a▓▓▓▓▓▓▓▓▓▓▓▓▓▓▓▓▓▓▓▓▓▓▓►
                                            EGFP ccatcctggtcgagctggacggcgacgtaaacggccacaagttcagcgtgtccggcgagggcgag
++++|++++|++++|++++|++++|++++|++++|++++|++++|++++|++++|++++|++++|    4485
ggtaggaccagctcgacctgccgctgcatttgccggtgttcaagtcgcacaggccgctcccgctc
      15              20              25              30
 P I L V E L D G D V N G H K F S V S G E G E
▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓►
                             EGFP
```

Figure 2 (cont.)

```
ggcgatgccacctacggcaagctgaccctgaagttcatctgcaccaccggcaagctgcccgtgcc
ccgctacggtggatgccgttcgactgggacttcaagtagacgtggtggccgttcgacgggcacgg
         35           40            45           50           55
     G  D  A  T  Y  G  K  L  T  L  K  F  I  C  T  T  G  K  L  P  V  P
                                    EGFP
```
4550

```
ctggcccaccctcgtgaccaccctgacctacggcgtgcagtgcttcagccgctaccccgaccaca
gaccgggtgggagcactggtgggactggatgccgcacgtcacgaagtcggcgatggggctggtgt
         60           65           70           75
     W  P  T  L  V  T  T  L  T  Y  G  V  Q  C  F  S  R  Y  P  D  H
                                    EGFP
```
4615

```
tgaagcagcacgacttcttcaagtccgccatgcccgaaggctacgtccaggagcgcaccatcttc
acttcgtcgtgctgaagaagttcaggcggtacgggcttccgatgcaggtcctcgcgtggtagaag
       80           85           90           95
   M  K  Q  H  D  F  F  K  S  A  M  P  E  G  Y  V  Q  E  R  T  I  F
                                    EGFP
```
4680

```
ttcaaggacgacggcaactacaagacccgcgccgaggtgaagttcgagggcgacaccctggtgaa
aagttcctgctgccgttgatgttctgggcgcggctccacttcaagctcccgctgtgggaccactt
     100          105          110          115          120
   F  K  D  D  G  N  Y  K  T  R  A  E  V  K  F  E  G  D  T  L  V  N
                                    EGFP
```
4745

```
ccgcatcgagctgaagggcatcgacttcaaggaggacggcaacatcctggggcacaagctggagt
ggcgtagctcgacttcccgtagctgaagttcctcctgccgttgtaggaccccgtgttcgacctca
        125          130          135          140
     R  I  E  L  K  G  I  D  F  K  E  D  G  N  I  L  G  H  K  L  E
                                    EGFP
```
4810

```
acaactacaacagccacaacgtctatatcatggccgacaagcagaagaacggcatcaaggtgaac
tgttgatgttgtcggtgttgcagatatagtaccggctgttcgtcttcttgccgtagttccacttg
          145          150          155          160
     Y  N  Y  N  S  H  N  V  Y  I  M  A  D  K  Q  K  N  G  I  K  V  N
                                    EGFP
```
4875

```
ttcaagatccgccacaacatcgaggacggcagcgtgcagctcgccgaccactaccagcagaacac
aagttctaggcggtgttgtagctcctgccgtcgcacgtcgagcggctggtgatggtcgtcttgtg
      165          170          175          180          185
   F  K  I  R  H  N  I  E  D  G  S  V  Q  L  A  D  H  Y  Q  Q  N  T
                                    EGFP
```
4940

Figure 2 (cont.)

```
     ccccatcggcgacggccccgtgctgctgcccgacaaccactacctgagcacccagtccgccctga
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5005
     ggggtagccgctgccggggcacgacgacgggctgttggtgatggactcgtgggtcaggcgggact
     ......190.......|.......195.......|.......200.......|.......205.......|
      P  I  G  D  G  P  V  L  L  P  D  N  H  Y  L  S  T  Q  S  A  L
     ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓>
                                     EGFP gcaaagaccccaacgagaagcgcgatcacatggtcctgctggagttcgtgaccgccgccgggatc
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5070
     cgtttctggggttgctcttcgcgctagtgtaccaggacgacctcaagcactggcggcggccctag
     ......210.......|.......215.......|.......220.......|.......225.......|
      S  K  D  P  N  E  K  R  D  H  M  V  L  L  E  F  V  T  A  A  G  I
     ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓>
                                     EGFP NotI
                                       |
     actctcggcatggacgagctgtacaagtaaagcggccgcgagctcgctgatcagcctcgactgtg
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5135
     tgagagccgtacctgctcgacatgttcatttcgccggcgctcgagcgactagtcggagctgacac
     .230.......|.......235.......|
      T  L  G  M  D  E  L  Y  K  ■
     ▓▓▓▓▓▓▓▓▓▓▓▓▓▓▓▓▓▓▓▓▓▓▓▓▓▓▓>                                 ▓▓▓▓▓
                  EGFP                                        bGH poly(A) signal ccttctagttgccagccatctgttgtttgcccctcccccgtgccttccttgaccctggaaggtgc
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5200
     ggaagatcaacggtcggtagacaacaaacggggagggggcacggaaggaactgggaccttccacg
     ▓▓▓▓▓▓▓▓▓▓▓▓▓▓▓▓▓▓▓▓▓▓▓▓▓▓▓▓▓▓▓ bGH poly(A) signal ▓▓▓▓▓▓▓▓▓▓▓▓▓▓▓ cactcccactgtcctttcctaataaaatgaggaaattgcatcgcattgtctgagtaggtgtcatt
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5265
     gtgagggtgacaggaaaggattatttactcctttaacgtagcgtaacagactcatccacagtaa
     ▓▓▓▓▓▓▓▓▓▓▓▓▓▓▓▓▓▓▓▓▓▓▓▓▓▓▓▓▓▓▓ bGH poly(A) signal ▓▓▓▓▓▓▓▓▓▓▓▓▓▓▓ ctattctggggggtggggtggggcaggacagcaaggggaggattgggaagacaatagcaggcat
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5330
     gataagaccccccacccccaccccgtcctgtcgttcccctcctaacccttctgttatcgtccgta
     ▓▓▓▓▓▓▓▓▓▓▓▓▓▓▓▓▓▓▓▓▓▓▓▓▓▓▓▓▓▓▓ bGH poly(A) signal ▓▓▓▓▓▓▓▓▓▓▓▓▓▓▓ gctggggatgcggtgggctctatggcttctgaggcggaaagaaccagctggggctcgatcctcta
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5395
     cgacccctacgccacccgagataccgaagactccgcctttcttggtcgaccccgagctaggagat
     ▓▓▓▓ bGH poly(A) signal ▓▓▓▓

AscI                                        SexAI*
         |                                            |
     gttggcgcgccgcgggagtcttctgggcaggcttaaaggctaacctggtgtgtgggcgttgtcct
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5460
     caaccgcgcggcgccctcagaagacccgtccgaatttccgattggaccacacacccgcaacagga gcaggggaattgaacaggtgtaaaattggagggacaagacttcccacagattttcggttttgtcg
     ++++-+-+-+-+-+-+-+|+-+-+-+-+-+-+-+|+-+-+-+-+-+-+-+|+-+-+-+-+-+-+-+|+-+-+-+-+-+-+-+|+-+-+-+-+-+-+-+|       5525
     cgtccccttaacttgtccacattttaacctccctgttctgaagggtgtctaaaagccaaaacagc
```

Figure 2 (cont.)

```
     ggaagttttttaataggggcaaataaggaaaatggggaggataggtagtcatctggggttttatgc
     ++++++++++++++++++++++++++++++++++++++++++++++++++++++++++++++++++   5590
     ccttcaaaaaattatccccgtttattccttttaccctcctatccatcagtagacccccaaaatacg agcaaaactacaggttattattgcttgtgatccgcctcggagtattttccatcgaggtagattaa
     ++++++++++++++++++++++++++++++++++++++++++++++++++++++++++++++++++   5655
     tcgttttgatgtccaataataacgaacactaggcggagcctcataaaaggtagctccatctaatt
                                                      ▓▓▓CR4 cut site▓▓▓ agacatgctcacccgagttttatactctcctgcttgagatccttactacagtatgaaattacagt
     ++++++++++++++++++++++++++++++++++++++++++++++++++++++++++++++++++   5720
     tctgtacgagtgggctcaaaatatgagaggacgaactctaggaatgatgtcatactttaatgtca
     ▓▓▓▓▓
     CR4 cut site NruI
         |
     gtcgcgagttagactatgtaagcagaatttttaatcattttaaagagcccagtacttcatatcca
     ++++++++++++++++++++++++++++++++++++++++++++++++++++++++++++++++++   5785
     cagcgctcaatctgatacattcgtcttaaaattagtaaaatttctcgggtcatgaagtataggt tttctcccgctccttctgcagccttatcaaaaggtattttagaacactcatttagccccatttt
     ++++++++++++++++++++++++++++++++++++++++++++++++++++++++++++++++++   5850
     aaagagggcgaggaagacgtcggaatagttttccataaaatcttgtgagtaaaatcggggtaaaa catttattatactggcttatccaaccccctagacagagcattggcattttccctttcctgatctta
     ++++++++++++++++++++++++++++++++++++++++++++++++++++++++++++++++++   5915
     gtaaataatatgaccgaataggttggggatctgtctcgtaaccgtaaaagggaaaggactagaat gaagtctgatgactcatgaaaccagacagattagttacatacaccacaaatcgaggctgtagctg
     ++++++++++++++++++++++++++++++++++++++++++++++++++++++++++++++++++   5980
     cttcagactactgagtactttggtctgtctaatcaatgtatgtggtgtttagctccgacatcgac gggcctcaacactgcagttcttttataactccttagtacacttttgttgatcctttgccttgat
     ++++++++++++++++++++++++++++++++++++++++++++++++++++++++++++++++++   6045
     cccggagttgtgacgtcaagaaaatattgaggaatcatgtgaaaaacaactaggaaacggaacta ccttaattttcagtgtctatcacctctcccgtcaggtggtgttccacatttgggcctattctcag
     ++++++++++++++++++++++++++++++++++++++++++++++++++++++++++++++++++   6110
     ggaattaaaagtcacagatagtggagagggcagtccaccacaaggtgtaaacccggataagagtc tccagggagttttacaacaatagatgtattgagaatccaacctaaagcttaactttccactccca
     ++++++++++++++++++++++++++++++++++++++++++++++++++++++++++++++++++   6175
     aggtccctcaaaatgttgttatctacataactcttaggttggatttcgaattgaaaggtgagggt tgaatgcctctctccttttctccatttataaactgagctattaaccattaatggtttccaggtg
     ++++++++++++++++++++++++++++++++++++++++++++++++++++++++++++++++++   6240
     acttacggagagaggaaaaagaggtaaatatttgactcgataattggtaattaccaaaggtccac gatgtctcctccccaatattacctgatgtatcttacatattgccaggctgatatttttaagacat
     ++++++++++++++++++++++++++++++++++++++++++++++++++++++++++++++++++   6305
     ctacagaggagggggttataatggactacatagaatgtaacggtccgactataaaattctgta
```

Figure 2 (cont.)

```
taaaaggtatatttcattattgagccacatggtattgattactgcttactaaaattttgtcattg
attttccatataaagtaataactcggtgtaccataactaatgacgaatgattttaaaacagtaac
```
6370

```
tacacatctgtaaaaggtggttccttttggaatgcaaagttcaggtgtttgttgtctttcctgac
atgtgtagacattttccaccaaggaaaaccttacgtttcaagtccacaaacaacagaaaggactg
```
6435

```
ctaaggtcttgtgagcttgtattttttctatttaagcagtgctttctcttggactggcttgactc
gattccagaacactcgaacataaaaagataaattcgtcacgaaagagaacctgaccgaactgag
```
6500

```
atggcattctacacgttattgctggtctaaatgtgattttgccaagcttcttcaggacctataat
taccgtaagatgtgcaataacgaccagattacactaaaacggttcgaagaagtcctggatatta
```
6565

```
tttgcttgacttgtagccaaacacaagtaaaatgattaagcaacaaatgtatttgtgaagcttgg
aaacgaactgaacatcggtttgtgttcatttactaattcgttgtttacataaacacttcgaacc
```
6630

```
ttttaggttgttgtgttgtgtgtgcttgtgctctataataatactatccaggggctggagaggt
aaaaatccaacaacacaacacacacgaacacgagatattattatgataggtccccgacctctcca
```
6695

```
                      BstAPI
                      |
ggctcggagttcaagagcacagactgctcttccagaagtcctgagttcaattcccagcaaccaca
ccgagcctcaagttctcgtgtctgacgagaaggtcttcaggactcaagttaagggtcgttggtgt
```
6760

```
tggtggctcacaaccatctgtaatgggatctgatgccctcttctggtgtgtctgaagaccacaag
accaccgagtgttggtagacattaccctagactacgggagaagaccacacagacttctggtgttc
```
6825

```
tgtattcacattaaataaataaatcctccttcttcttctttttttttttttaaagagaatactg
acataagtgtaatttatttattaggaggaagaagaagaaaaaaaaaaaaatttctcttatgac
```
6890

```
tctccagtagaatttactgaagtaatgaaatactttgtgtttgttccaatatggtagccaataat
agaggtcatcttaaatgacttcattactttatgaaacacaaacaaggttataccatcggttatta
```
6955

```
caaattactctttaagcactggaaatgttaccaaggaactaattttatttgaagtgtaactgtg
gtttaatgagaaattcgtgacctttacaatggttccttgattaaaaataaacttcacattgacac
```
7020

```
gacagaggagccataactgcagacttgtgggatacagaagaccaatgcagactttaatgtctttt
ctgtctcctcggtattgacgtctgaacaccctatgtcttctggttacgtctgaaattacagaaaa
```
7085

Figure 2 (cont.)

```
                                                   NheI     BmtI
ctcttacactaagcaataaagaaataaaaattgaacttctagtatcctatttgttaaactgctag
                                                                        7150
gagaatgtgattcgttatttcttattttaacttgaagatcataggataaacaatttgacgatc ctttacttaacttttgtgcttcatctatacaaagctgaaagctaagtctgcagccattactaaac
                                                                        7215
gaaatgaattgaaaacacgaagtagatatgtttcgactttcgattcagacgtcggtaatgatttg atgaaagcaagtaatgataattttggatttcaaaaatgtagggccagagtttagccagccagtgg
                                                                        7280
tactttcgttcattactattaaaacctaaagttttacatcccggtctcaaatcggtcggtcacc tggtgcttgcctttatgcctttaatcccagcactctggaggcagagacaggcagatctctgagtt
                                                                        7345
accacgaacggaaatacggaaattagggtcgtgagacctccgtctctgtccgtctagagactcaa BpiI
tgagcccagcctggtctacacatcaagttctatctaggatagccaggaatacacacagaaaccct
                                                                        7410
actcgggtcggaccagatgtgtagttcaagatagatcctatcggtccttatgtgtgtctttggga BpiI
gttggggagggggggctctgagatttcataaaattataattgaagcattccctaatgagccactat
                                                                        7475
caaccccctcccccgagactctaaagtattttaatattaacttcgtaagggattactcggtgata ggatgtggctaaatccgtctacctttctgatgagatttgggtattatttttctgtctctgctgt
                                                                        7540
cctacaccgatttaggcagatggaaagactactctaaacccataataaaaagacagagacgaca tggttgggtcttttgacactgtgggctttctttaaagcctccttccctgccatgtggtctcttgt
                                                                        7605
accaacccagaaaactgtgacacccgaaagaaatttcggaggaagggacggtacaccagagaaca ttgctactaacttcccatggcttaaatggcatggcttttgccttctaagggcagctgctgagat
                                                                        7670
aacgatgattgaagggtaccgaatttaccgtaccgaaaaacggaagattcccgtcgacgactcta ttgcagcctgatttccagggtggggttgggaaatctttcaaacactaaaattgtcctttaatttt
                                                                        7735
aacgtcggactaaaggtcccaccccaacccttttagaaagtttgtgatttaacaggaaattaaaa tttttaaaaatgggttatataataaacctcataaatagttatgaggagtgaggtggactaat
                                                                        7800
aaaaaattttttacccaatatattatttggagtatttatcaatactcctcactccacctgatta attaaatgagtccctcccctataaaagagctattaaggcttttgtcttatacttaactttttt
                                                                        7865
taatttactcagggaggggatattttctcgataattccgaaaaacagaatatgaattgaaaaaaa
```

Figure 2 (cont.)

```
ttaaatgtggtatctttagaaccaagggtcttagagttttagtatacagaaactgttgcatcgct
                                                                                    7930
aatttacaccatagaaatcttggttcccagaatctcaaaatcatatgtctttgacaacgtagcga taatcagattttctagtttcaaatccagagaatccaaattcttcacagccaaagtcaaattaaga
                                                                                    7995
attagtctaaaagatcaaagtttaggtctcttaggtttaagaagtgtcggtttcagtttaattct atttctgacttttaatgttaatttgcttactgtgaatataaaaatgatagcttttcctgaggcag
                                                                                    8060
taaagactgaaaattacaattaaacgaatgacacttatattttactatcgaaaaggactccgtc ggtctcactatgtatctctgcctgatctgcaacaagatatgtagactaaagttctgcctgctttt
                                                                                    8125
ccagagtgatacatagagacggactagacgttgttctatacatctgatttcaagacggacgaaaa gtctcctgaatactaaggttaaaatgtagtaatacttttggaacttgcaggtcagattcttttat
                                                                                    8190
cagaggacttatgattccaattttacatcattatgaaaaccttgaacgtccagtctaagaaaata aggggacacactaagggagcttgggtgatagttggtaaatgtgtttcaagtgatgaaaacttga
                                                                                    8255
tcccctgtgtgattccctcgaacccactatcaaccattttacacaaagttcactacttttgaact attattatcaccgcaacctactttttaaaaaaaaagccaggcctgttagagcatgcttaaggga
                                                                                    8320
taataatagtggcgttggatgaaaattttttttttcggtccggacaatctcgtacgaattccct
```
BamHi site in middle of locus

```
     AvrII
     |
tccctaggacttgctgagcacacaagagtagttacttggcaggctcctggtgagagcatatttca
                                                                                    8385
agggatcctgaacgactcgtgtgttctcatcaatgaaccgtccgaggaccactctcgtataaagt
```
BamHi site in middle of locus

```
                             BstEII
                             |
aaaaacaaggcagacaaccaagaaactacagttaaggttacctgtctttaaaccatctgcatata
                                                                                    8450
ttttgttccgtctgttggttctttgatgtcaattccaatggacagaaatttggtagacgtatat cacagggatattaaaatattccaaataatatttcattcaagttttcccccatcaaattgggacat
                                                                                    8515
gtgtccctataattttataaggtttattataaagtaagttcaaaaggggtagtttaaccctgta ggatttctccggtgaataggcagagttggaaactaaacaaatgttggttttgtgatttgtgaaat
                                                                                    8580
cctaaagaggccacttatccgtctcaacctttgatttgtttacaaccaaaacactaaacacttta
```

Figure 2 (cont.)

```
tgttttcaagtgatagttaaagcccatgagatacagaacaaagctgctatttcgaggtctcttgg
                                                                            8645
acaaaagttcactatcaatttcgggtactctatgtcttgtttcgacgataaagctccagagaacc tttatactcagaagcacttctttgggtttccctgcactatcctgatcatgtgctaggcctacctt
                                                                            8710
aaatatgagtcttcgtgaagaaacccaaagggacgtgataggactagtacacgatccggatggaa NdeI
                                              |
aggctgattgttgttcaaataaacttaagtttcctgtcaggtgatgtcatatgatttcatatatc
                                                                            8775
tccgactaacaacaagtttatttgaattcaaaggacagtccactacagtatactaaagtatatag aaggcaaaacatgttatatatgttaaacatttgtacttaatgtgaaagttaggtctttgtgggtt
                                                                            8840
ttccgttttgtacaatatatacaatttgtaaacatgaattacactttcaatccagaaacacccaa ttgattttaattttcaaaacctgagctaaataagtcattttacatgtcttacatttggtggaa
                                                                            8905
aactaaaaattaaaagttttggactcgatttattcagtaaaaatgtacagaatgtaaaccacctt ttgtataattgtggtttgcaggcaagactctctgacctagtaaccctacctatagagcactttgc
                                                                            8970
aacatattaacaccaaacgtccgttctgagagactggatcattgggatggatatctcgtgaaacg tgggtcacaagtctaggagtcaagcatttcaccttgaagttgagacgttttgttagtgtatacta
                                                                            9035
acccagtgttcagatcctcagttcgtaaagtggaacttcaactctgcaaaacaatcacatatgat gtttatatgttggaggacatgtttatccagaagatattcaggactattttgactgggctaagga
                                                                            9100
caaatatacaacctcctgtacaaataggtcttctataagtcctgataaaaactgacccgattcct attgattctgattagcactgttagtgagcattgagtggcctttaggcttgaattggagtcacttg
                                                                            9165
taactaagactaatcgtgacaatcactcgtaactcaccggaaatccgaacttaacctcagtgaac tatatctcaaataatgctggccttttttaaaaagcccttgttctttatcaccctgttttctacat
                                                                            9230
atatagagtttattacgaccggaaaaaattttcgggaacaagaaatagtgggacaaaagatgta aattttgttcaaagaaatacttgtttggatctccttttgacaacaatagcatgttttcaagcca
                                                                            9295
ttaaaacaagtttctttatgaacaaacctagaggaaaactgttgttatcgtacaaaagttcggt tatttttttcctttttttttttttttggttttttcgagacagggtttctctgtatagccctgg
                                                                            9360
ataaaaaaaggaaaaaaaaaaaaaaaaccaaaaagctctgtcccaagagacatatcgggacc ctgtcctggaactcactttgtagaccaggctggcctcgaactcagaaatccgcctgcctctgcct
                                                                            9425
gacaggaccttgagtgaaacatctggtccgaccggagcttgagtctttaggcggacggagacgga
```

Figure 2 (cont.)

```
cctgagtgccgggattaaaggcgtgcaccaccacgcctggctaagttggatattttgtatataac
++++|++++|++++|++++|++++|++++|++++|++++|++++|++++|++++|++++|++++|    9490
ggactcacggccctaatttccgcacgtggtggtgcggaccgattcaacctataaaacatatattg tataaccaatactaactccactgggtggattttaattcagtcagtagtcttaagtggtctttat
++++|++++|++++|++++|++++|++++|++++|++++|++++|++++|++++|++++|++++|    9555
atattggttatgattgaggtgacccacctaaaaattaagtcagtcatcagaattcaccagaaata tggcccttcattaaaatctactgttcactctaacagaggctgttggtactagtggcacttaagca
++++|++++|++++|++++|++++|++++|++++|++++|++++|++++|++++|++++|++++|    9620
accgggaagtaattttagatgacaagtgagattgtctccgacaaccatgatcaccgtgaattcgt acttcctacggatatactagcagattaagggtcagggatagaaactagtctagcgttttgtatac
++++|++++|++++|++++|++++|++++|++++|++++|++++|++++|++++|++++|++++|    9685
tgaaggatgcctatatgatcgtctaattcccagtccctatctttgatcagatcgcaaaacatatg SgrDI
                                                              |
ctaccagctttatactaccttgttctgatagaaatatttcaggacatctagcttatcgatccgtc
++++|++++|++++|++++|++++|++++|++++|++++|++++|++++|++++|++++|++++|    9750
gatggtcgaaatatgatggaacaagactatctttataaagtcctgtagatcgaatagctaggcag gacggtatcgataagcttgatatcgaattctaccgggtaggggaggcgcttttccaaggcagtct
++++|++++|++++|++++|++++|++++|++++|++++|++++|++++|++++|++++|++++|    9815
ctgccatagctattcgaactatagcttaagatgggccatccctccgcgaaaaggttccgtcaga
                                              [ PGK promoter ]  > gagcatgcgcttagcagcccgctggcacttggcgctacacaagtggcctytggcctcgcacaca
++++|++++|++++|++++|++++|++++|++++|++++|++++|++++|++++|++++|++++|    9880
ctcgtacgcgaatcgtcgggcgaccgtgaaccgcgatgtgttcaccggaraccggagcgtgtgt
                               PGK promoter                      >

AgeI
          |
ttccacatccaccggtaggcgccaaccggctccgttctttggtggccccttcgcgccaccttctw
++++|++++|++++|++++|++++|++++|++++|++++|++++|++++|++++|++++|++++|    9945
aaggtgtaggtggccatccgcggttggccgaggcaagaaaccaccggggaagcgcggtggaagaw
                               PGK promoter                      > ctcctcccctagtcaggaagttccccccgccccgcagctcgcgtcgtsaggacgtgacaaatgg
++++|++++|++++|++++|++++|++++|++++|++++|++++|++++|++++|++++|++++|   10,010
gaggaggggatcagtccttcaagggggggcgggcgtcgagcgcagcastcctgcactgtttacc
                               PGK promoter                      > aagtagcacgtctcactagtctcgtcagatggacagcaccgctgagcaatggaagcgggtaggcc
++++|++++|++++|++++|++++|++++|++++|++++|++++|++++|++++|++++|++++|   10,075
ttcatcgtgcagagtgatcagagcagtctacctgtcgtggcgactcgttaccttcgcccatccgg
                               PGK promoter                      >
```

Figure 2 (cont.)

```
tttggggcagcggccaatagcagctttgctccttcgctttctgggctcagaggctgggaaggggt
aaaccccgtcgccggttatcgtcgaaacgaggaagcgaaagacccgagtctccgacccttcccca    10,140
                          PGK promoter gggtccggggcgggctcaggggcgggctcaggggcggggcgggcgcccgaaggtcctccggagg
cccaggccccgcccgagtccccgcccgagtccccgccccgcccgcgggcttccaggaggcctcc    10,205
                          PGK promoter cccggcattctgcacgcttcaaaagcgcacgtctgccgcgctgttctcctcttcctcatctccgg
gggccgtaagacgtgcgaagttttcgcgtgcagacggcgcgacaagaggagaaggagtagaggcc    10,270
                          PGK promoter gcctttcgacctgcaggtcctcgccatggatcctgatgatgttgttattcttctaatcttttgta
cggaaagctggacgtccaggagcggtacctaggactactacaacaataagaagattagaaaacat    10,335
PGK promoter SexAI*
tggaaaacttttcttcgtaccacgggactaaacctggttatgtagattccattcaaaaaggtata
accttttgaaaagaagcatggtgccctgatttggaccaatacatctaaggtaagttttttccatat    10,400 caaaagccaaaatctggtacacaaggaaattatgacgatgattggaaagggttttatagtaccga
gttttcggttttagaccatgtgttcctttaatactgctactaaccttttcccaaaatatcatggct    10,465 caataaatacgacgctgcgggatactctgtagataatgaaaacccgctctctggaaaagctggag
gttatttatgctgcgacgccctatgagacatctattacttttgggcgagagaccttttcgacctc    10,530 gcgtggtcaaagtgacgtatccaggactgacgaaggttctcgcactaaaagtggataatgccgaa
cgcaccagtttcactgcataggtcctgactgcttccaagagcgtgattttcacctattacggctt    10,595 actattaagaaagagttaggtttaagtctcactgaaccgttgatggagcaagtcggaacggaaga
tgataattctttctcaatccaaattcagagtgacttggcaactacctcgttcagccttgccttct    10,660

BbvCI
gtttatcaaaaggttcggtgatggtgcttcgcgtgtagtgctcagccttcccttcgctgagggga
caaatagttttccaagccactaccacgaagcgcacatcacgagtcggaagggaagcgactcccct    10,725 gttctagcgttgaatatattaataactgggaacaggcgaaagcgttaagcgtagaacttgagatt
caagatcgcaacttatataattattgacccttgtccgctttcgcaattcgcatcttgaactctaa    10,790
```

Figure 2 (cont.)

```
aattttgaaacccgtggaaaacgtggccaagatgcgatgtatgagtatatggctcaagcctgtgc
ttaaaactttgggcaccttttgcaccggttctacgctacatactcatataccgagttcggacacg
```
10,855

```
aggaaatcgtgtcaggcgatctctttgtgaaggaaccttacttctgtggtgtgacataattggac
tcctttagcacagtccgctagagaaacacttccttggaatgaagacaccacactgtattaacctg
```
10,920

```
aaactacctacagagatttaaagctctaaggtaaatataaaattttaagtgtataatgtgttaa
tttgatggatgtctctaaatttcgagattccatttatattttaaaaattcacatattacacaatt
```
10,985

|———————————— small t intron ——————————————

```
actactgattctaattgtttgtgtattttagattccaacctatggaactgatgaatgggagcagt
tgatgactaagattaacaaacacataaaatctaaggttggataccttgactacttaccctcgtca
```
11,050

——————————— small t intron ——————————|

```
ggtggaatgcagatcctagagctcgctgatcagcctcgactgtgccttctagttgccagccatct
ccaccttacgtctaggatctcgagcgactagtcggagctgacacggaagatcaacggtcggtaga
```
11,115 bGH poly(A) signal

```
gttgtttgcccctcccccgtgccttccttgaccctggaaggtgccactcccactgtcctttccta
caacaaacggggagggggcacggaaggaactgggaccttccacggtgagggtgacaggaaaggat
```
11,180 bGH poly(A) signal

```
ataaaatgaggaaattgcatcgcattgtctgagtaggtgtcattctattctggggggtggggtgg
tattttactcctttaacgtagcgtaacagactcatccacagtaagataagaccccccaccccacc
```
11,245 bGH poly(A) signal

```
ggcaggacagcaaggggggaggattgggaagacaatagcaggcatgctggggatgcggtgggctct
ccgtcctgtcgttccccctcctaacccttctgttatcgtccgtacgacccctacgccacccgaga
```
11,310 bGH poly(A) signal

TliI
AbsI
XhoI
PspXI
PaeR7I     Acc65I     KpnI

```
atggcttctgaggcggaaagaaccagctggggctcgacctcgagggggggcccggtacccagctt
taccgaagactccgcctttcttggtcgaccccgagctgagctccccccgggccatgggtcgaa
```
11,375 bGH poly(A) signal

Figure 2 (cont.)

```
ttgttccctttagtgagggttaattgcgcgcttggcgtaatcatggtcatagctgtttcctgtgt
++++++++++++++++++++++++++++++++++++++++++++++++++++++++++++++++++    11,440
aacaagggaaatcactcccaattaacgcgcgaaccgcattagtaccagtatcgacaaaggacaca
        < T3 promoter ]                              ◄ M13 rev ► gaaattgttatccgctcacaattccacacaacatacgagccggaagcataaagtgtaaagcctgg
++++++++++++++++++++++++++++++++++++++++++++++++++++++++++++++++++    11,505
ctttaacaataggcgagtgttaaggtgtgttgtatgctcggccttcgtatttcacatttcggacc
     lac operator         <  -10  |                         -35  |
                                       lac promoter ggtgcctaatgagtgagctaactcacattaattgcgttgcgctcactgcccgctttccagtcggg
++++++++++++++++++++++++++++++++++++++++++++++++++++++++++++++++++    11,570
ccacggattactcactcgattgagtgtaattaacgcaacgcgagtgacgggcgaaaggtcagccc
              CAP binding site aaacctgtcgtgccagctgcattaatgaatcggccaacgcgcggggagaggcggtttgcgtattg
++++++++++++++++++++++++++++++++++++++++++++++++++++++++++++++++++    11,635
tttggacagcacggtcgacgtaattacttagccggttgcgcgcccctctccgccaaacgcataac ggcgctcttccgcttcctcgctcactgactcgctgcgctcggtcgttcggctgcggcgagcggta
++++++++++++++++++++++++++++++++++++++++++++++++++++++++++++++++++    11,700
ccgcgagaaggcgaaggagcgagtgactgagcgacgcgagccagcaagccgacgccgctcgccat tcagctcactcaaaggcggtaatacggttatccacagaatcaggggataacgcaggaaagaacat
++++++++++++++++++++++++++++++++++++++++++++++++++++++++++++++++++    11,765
agtcgagtgagtttccgccattatgccaataggtgtcttagtccctattgcgtcctttcttgta gtgagcaaaaggccagcaaaaggccaggaaccgtaaaaaggccgcgttgctggcgttttccata
++++++++++++++++++++++++++++++++++++++++++++++++++++++++++++++++++    11,830
cactcgttttccggtcgttttccggtccttggcattttccggcgcaacgaccgcaaaaaggtat
                                                              < ori ggctccgcccccctgacgagcatcacaaaaatcgacgctcaagtcagaggtggcgaaacccgaca
++++++++++++++++++++++++++++++++++++++++++++++++++++++++++++++++++    11,895
ccgaggcggggggactgctcgtagtgttttagctgcgagttcagtctccaccgctttgggctgt
<━━━━━━━━━━━━━━━━━━━━━━━━━━━━━ ori ━━━━━━━━━━━━━━━━━━━━━━━━━━━━━━ ggactataaagataccaggcgtttccccctggaagctccctcgtgcgctctcctgttccgaccct
++++++++++++++++++++++++++++++++++++++++++++++++++++++++++++++++++    11,960
cctgatatttctatggtccgcaaaggggggaccttcgagggagcacgcgagaggacaaggctggga
<━━━━━━━━━━━━━━━━━━━━━━━━━━━━━ ori ━━━━━━━━━━━━━━━━━━━━━━━━━━━━━━ gccgcttaccggatacctgtccgcctttctcccttcgggaagcgtggcgctttctcatagctcac
++++++++++++++++++++++++++++++++++++++++++++++++++++++++++++++++++    12,025
cggcgaatggcctatggacaggcggaagagggaagcccttcgcaccgcgaaagagtatcgagtg
<━━━━━━━━━━━━━━━━━━━━━━━━━━━━━ ori ━━━━━━━━━━━━━━━━━━━━━━━━━━━━━━
```

Figure 2 (cont.)

```
        gctgtaggtatctcagttcggtgtaggtcgttcgctccaagctgggctgtgtgcacgaacccccc
        ++++|++++|++++|++++|++++|++++|++++|++++|++++|++++|++++|++++|++++|    12,090
        cgacatccatagagtcaagccacatccagcaagcgaggttcgaccccgacacacgtgcttgggggg
        <───────────────────────────── ori ───────────────────────────── gttcagcccgaccgctgcgccttatccggtaactatcgtcttgagtccaacccggtaagacacga
        ++++|++++|++++|++++|++++|++++|++++|++++|++++|++++|++++|++++|++++|    12,155
        caagtcgggctggcgacgcggaataggccattgatagcagaactcaggttgggccattctgtgct
        <───────────────────────────── ori ───────────────────────────── cttatcgccactggcagcagccactggtaacaggattagcagagcgaggtatgtaggcggtgcta
        ++++|++++|++++|++++|++++|++++|++++|++++|++++|++++|++++|++++|++++|    12,220
        gaatagcggtgaccgtcgtcggtgaccattgtcctaatcgtctcgctccatacatccgccacgat
        <───────────────────────────── ori ───────────────────────────── cagagttcttgaagtggtggcctaactacggctacactagaaggacagtatttggtatctgcgct
        ++++|++++|++++|++++|++++|++++|++++|++++|++++|++++|++++|++++|++++|    12,285
        gtctcaagaacttcaccaccggattgatgccgatgtgatcttcctgtcataaaccatagacgcga
        <───────────────────────────── ori ───────────────────────────── ctgctgaagccagttaccttcggaaaaagagttggtagctcttgatccggcaaacaaaccaccgc
        ++++|++++|++++|++++|++++|++++|++++|++++|++++|++++|++++|++++|++++|    12,350
        gacgacttcggtcaatggaagccttttctcaaccatcgagaactaggccgtttgtttggtggcg
        <───────────────────────────── ori ───────────────────────────── tggtagcggtggttttttgtttgcaagcagcagattacgcgcagaaaaaaaggatctcaagaag
        ++++|++++|++++|++++|++++|++++|++++|++++|++++|++++|++++|++++|++++|    12,415
        accatcgccaccaaaaaaacaaacgttcgtcgtctaatgcgcgtctttttttcctagagttcttc
        <───────────────────────────── ori ───────────────────────────── atcctttgatcttttctacggggtctgacgctcagtggaacgaaaactcacgttaagggattttg
        ++++|++++|++++|++++|++++|++++|++++|++++|++++|++++|++++|++++|++++|    12,480
        taggaaactagaaaagatgccccagactgcgagtcaccttgcttttgagtgcaattccctaaaac gtcatgagattatcaaaaaggatcttcacctagatccttttaaattaaaaatgaagttttaaatc
        ++++|++++|++++|++++|++++|++++|++++|++++|++++|++++|++++|++++|++++|    12,545
        cagtactctaatagttttcctagaagtggatctaggaaaatttaattttacttcaaaatttag aatctaaagtatatatgagtaaacttggtctgacagttaccaatgcttaatcagtgaggcaccta
        ++++|++++|++++|++++|++++|++++|++++|++++|++++|++++|++++|++++|++++|    12,610
        ttagatttcatatatactcatttgaaccagactgtcaatggttacgaattagtcactccgtggat
                                               285            280
                                            W  H  K  I  L  S  A  G  I
                                           <──────────────────────────
                                                      AmpR
```

Figure 2 (cont.)

```
      tctcagcgatctgtctatttcgttcatccatagttgcctgactccccgtcgtgtagataactacg
      ++++|++++|++++|++++|++++|++++|++++|++++|++++|++++|++++|++++|++++|+++++       12,675
      agagtcgctagacagataaagcaagtaggtatcaacggactgagggcagcacatctattgatgc
      ........275........|........270........|........265........|........260........|.....
          E   A   I   Q   R   N   R   E   D   M   T   A   Q   S   G   T   T   Y   I   V   V
   <──────────────────────────────────────────────────────────────────────
                                        AmpR atacgggagggcttaccatctggccccagtgctgcaatgataccgcgagacccacgctcaccggc
      ++++|++++|++++|++++|++++|++++|++++|++++|++++|++++|++++|++++|++++|++++       12,740
      tatgccctcccgaatggtagaccggggtcacgacgttactatggcgctctgggtgcgagtggccg
      ........255........|........250........|........245........|........240........|........235
          I   R   S   P   K   G   D   P   G   L   A   A   I   I   G   R   S   G   R   E   G   A
   <──────────────────────────────────────────────────────────────────────
                                        AmpR tccagatttatcagcaataaaccagccagccggaagggccgagcgcagaagtggtcctgcaactt
      ++++|++++|++++|++++|++++|++++|++++|++++|++++|++++|++++|++++|++++|+++++       12,805
      aggtctaaatagtcgttatttggtcggtcggccttcccggctcgcgtcttcaccaggacgttgaa
      ........230........|........225........|........220........|........215........|.....
          G   S   K   D   A   I   F   W   G   A   P   L   A   S   R   L   L   P   G   A   V   K
   <──────────────────────────────────────────────────────────────────────
                                        AmpR tatccgcctccatccagtctattaattgttgccgggaagctagagtaagtagttcgccagttaat
      ++++|++++|++++|++++|++++|++++|++++|++++|++++|++++|++++|++++|++++|+++++       12,870
      ataggcggaggtaggtcagataattaacaacggcccttcgatctcattcatcaagcggtcaatta
      ........210........|........205........|........200........|........195........|.....
          D   A   E   M   W   D   I   L   Q   Q   R   S   A   L   T   L   L   E   G   T   L
   <──────────────────────────────────────────────────────────────────────
                                        AmpR agtttgcgcaacgttgttgccattgctacaggcatcgtggtgtcacgctcgtcgtttggtatggc
      ++++|++++|++++|++++|++++|++++|++++|++++|++++|++++|++++|++++|++++|+++++       12,935
      tcaaacgcgttgcaacaacggtaacgatgtccgtagcaccacagtgcgagcagcaaaccataccg
      ........190........|........185........|........180........|........175........|........170
          L   K   R   L   T   T   A   M   A   V   P   M   T   T   D   R   E   D   N   P   I   A
   <──────────────────────────────────────────────────────────────────────
                                        AmpR ttcattcagctccggttcccaacgatcaaggcgagttacatgatcccccatgttgtgcaaaaaag
      ++++|++++|++++|++++|++++|++++|++++|++++|++++|++++|++++|++++|++++|+++++       13,000
      aagtaagtcgaggccaaggggttgctagttccgctcaatgtactaggggtacaacacgttttttc
      ........165........|........160........|........155........|........150........|.....
          E   N   L   E   P   E   W   R   D   L   R   T   V   H   D   G   M   N   H   L   F   A
   <──────────────────────────────────────────────────────────────────────
                                        AmpR PvuI
                                                |
      cggttagctccttcggtcctccgatcgttgtcagaagtaagttggccgcagtgttatcactcatg
      ++++|++++|++++|++++|++++|++++|++++|++++|++++|++++|++++|++++|++++|+++++       13,065
      gccaatcgaggaagccaggaggctagcaacagtcttcattcaaccggcgtcacaatagtgagtac
      ........145........|........140........|........135........|........130........|.....
          T   L   E   K   P   G   G   I   T   T   L   L   L   N   A   A   T   N   D   S   M
   <──────────────────────────────────────────────────────────────────────
                                        AmpR
```

Figure 2 (cont.)

```
gttatggcagcactgcataattctcttactgtcatgccatccgtaagatgcttttctgtgactgg
caataccgtcgtgacgtattaagagaatgacagtacggtaggcattctacgaaaagacactgacc
     125            120            115            110            105
  T  I  A  A  S  C  L  E  R  V  T  M  G  D  T  L  H  K  E  T  V  P
<────────────────────────────────────────────────────────────────────
                              AmpR
```
13,130

```
tgagtactcaaccaagtcattctgagaatagtgtatgcggcgaccgagttgctcttgcccggcgt
actcatgagttggttcagtaagactcttatcacatacgccgctggctcaacgagaacgggccgca
     100             95             90             85
  S  Y  E  V  L  D  N  Q  S  Y  H  I  R  R  G  L  Q  E  Q  G  A  D
<────────────────────────────────────────────────────────────────────
                              AmpR
```
13,195

```
caatacgggataataccgcgccacatagcagaactttaaaagtgctcatcattggaaaacgttct
gttatgccctattatggcgcggtgtatcgtcttgaaattttcacgagtagtaaccttttgcaaga
      80             75             70             65
  I  R  S  L  V  A  G  C  L  L  V  K  F  T  S  M  M  P  F  R  E
<────────────────────────────────────────────────────────────────────
                              AmpR
```
13,260

```
tcggggcgaaaactctcaaggatcttaccgctgttgagatccagttcgatgtaacccactcgtgc
agccccgcttttgagagttcctagaatggcgacaactctaggtcaagctacatgggtgagcacg
      60             55             50             45             40
  E  P  R  F  S  E  L  I  K  G  S  N  L  D  L  E  I  Y  G  V  R  A
<────────────────────────────────────────────────────────────────────
                              AmpR
```
13,325

```
acccaactgatcttcagcatcttttactttcaccagcgtttctgggtgagcaaaaacaggaaggc
tgggttgactagaagtcgtagaaaatgaaagtggtcgcaaagacccactcgttttgtccttccg
      35             30             25             20
  G  L  Q  D  E  A  D  K  V  K  V  L  T  E  P  H  A  F  V  P  L  C
                                               │  signal sequence
<────────────────────────────────────────────────────────────────────
                              AmpR
```
13,390

```
aaaatgccgcaaaaagggaataagggcgacacggaaatgttgaatactcatactcttccttttt
ttttacggcgttttttcccttattcccgctgtgcctttacaacttatgagtatgagaaggaaaaa
      15             10              5              1
  F  A  A  F  F  P  I  L  A  V  R  F  H  Q  I  S  M
                  signal sequence                        < AmpR promoter
<────────────────────────────────────────────────────────────────────
                              AmpR
```
13,455

```
caatattattgaagcatttatcagggttattgtctcatgagcggatacatatttgaatgtattta
gttataataacttcgtaaatagtcccaataacagagtactcgcctatgtataaacttacataaat
<────────────────────────────────────────────────────────────────────
                          AmpR promoter
```
13,520

Figure 2 (cont.)

```
                                            CspCI
         gaaaaataaacaaatagggggttccgcgcacatttccccgaaaagtgccacctaaattgtaagcgt
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,585
         cttttatttgtttatccccaaggcgcgtgtaaagggcttttcacggtggatttaacattcgca
      <─────AmpR promoter──────────────┤               <──── f1 ori ────

CspCI
         taatattttgttaaaattcgcgttaaattttttgttaaatcagctcattttttaaccaataggccg
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,650
         attataaaacaattttaagcgcaatttaaaaacaatttagtcgagtaaaaaattggttatccggc
      <──────────────────────────── f1 ori ────────────────────────────── aaatcggcaaaatcccttataaatcaaagaatagaccgagatagggttgagtgttgttccagtt
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,715
         tttagccgttttagggaatatttagttttcttatctggctctatcccaactcacaacaaggtcaa
      <──────────────────────────── f1 ori ──────────────────────────────

AloI                               AloI
         tggaacaagagtccactattaaagaacgtggactccaacgtcaaagggcgaaaaaccgtctatca
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,780
         accttgttctcaggtgataattcttgcacctgaggttgcagtttcccgcttttggcagatagt
      <──────────────────────────── f1 ori ──────────────────────────────

BsaAI
         gggcgatggcccactacgtgaaccatcaccctaatcaagttttttggggtcgaggtgccgtaaag
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,845
         cccgctaccgggtgatgcacttggtagtgggattagttcaaaaaacccagctccacggcatttc
      <──────────────────────────── f1 ori ────────────────────────────── cactaaatcggaaccctaaagggagccccgatttagagcttgacggggaaagccggcgaacgtg
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,910
         gtgatttagccttgggatttccctcgggggctaaatctcgaactgccccttttcggccgcttgcac
      <──────────────────────────── f1 ori ────────────────────────────── gcgagaaaggaagggaagaaagcgaaaggagcgggcgctagggcgctggcaagtgtagcggtcac
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  13,975
         cgctctttccttcccttctttcgcttcctcgcccgcgatcccgcgaccgttcacatcgccagtg
      <──────────────────────────── f1 ori ────────────────────────────── gctgcgcgtaaccaccacacccgccgcgcttaatgcgccgctacagggcgcgtcccattcgccat
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  14,040
         cgacgcgcattggtggtgtgggcggcgcgaattacgcggcgatgtcccgcgcagggtaagcggta
      <──────────────────────────── f1 ori ──────────────────────────────

PvuI
         tcaggctgcgcaactgttgggaagggcgatcggtgcgggcctcttcgctattacgccagctggcg
         ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖  14,105
         agtccgacgcgttgacaacccttcccgctagccacgcccggagaagcgataatgcggtcgaccgc
```

Figure 2 (cont.)

```
aaaggggatgtgctgcaaggcgattaagttgggtaacgccagggttttcccagtcacgacgttg
                                                                              14,170
tttccccctacacgacgttccgctaattcaacccattgcggtcccaaaagggtcagtgctgcaac
                                                            M13 fwd taaaacgacggccagtgagcgcgcgtaatacgactcactatagggcgaattggagctccccgcgg
                                                                              14,235
attttgctgccggtcactcgcgcgcattatgctgagtgatatcccgcttaacctcgaggggcgcc
     M13 fwd                  T7 promoter caggccctccgagcgtggtggagccgttctgtgagacagccgggtacgagtcgtgacgctggaag
                                                                              14,300
gtccgggaggctcgcaccacctcggcaagacactctgtcgcccatgctcagcactgcgaccttc RsrII
gggcaagcgggtggtgggcaggaatgcggtccgccctgcagcaaccggaggggagggagaaggg
                                                                              14,365
cccgttcgcccaccacccgtccttacgccaggcgggacgtcgttggcctcccccctccctcttccc AfeI
agcggaaaagtctccaccggacgcggccatggctcggggggggggggcagcggaggagcgcttc
                                                                              14,430
tcgccttttcagaggtggcctgcgccggtaccgagccccccccccgtcgcctcctcgcgaag ZraI  AatII
cggccgacgtctcgtcgctgattggcttcttttcctcccgccgtgtgtgaaaacacaaatggcgt
                                                                              14,495
gccggctgcagagcagcgactaaccgaagaaaaggagggcggcacacactttgtgtttaccgca gttttggttggcgtaaggcgcctgtcagttaacggcagccggagtgcgcagccgccggcagcctc
                                                                              14,560
caaaaccaaccgcattccgcggacagtcaattgccgtcggcctcacgcgtcggcggccgtcggag gctctgcccactgggtggggcgggaggtaggtggggtgaggcgagctggacgtgcgggcgcggtc
                                                                              14,625
cgagacgggtgacccaccccgccctccatccaccccactccgctcgacctgcacgcccgcgccag MauBI      NotI
ggcctctggcggggcggggaggggagggagggtcagcgaaagtagctcgcgcgcgagcggccgc
                                                                              14,690
ccggagaccgccccgcccctccctcccagtcgctttcatcgagcgcgcgctcgccggcg ccacccctcccttcctctggggagtcgttttacccgccgccggccgggcctcgtcgtctgattg
                                                                              14,755
ggtgggaggggaaggagacccctcagcaaaatgggcggcggccggcccggagcagcagactaac gctctcggggcccagaaaactggcccttgccattggctcgtgttcgtgcaagttgagtccatccg
                                                                              14,820
cgagagccccgggtcttttgaccgggaacggtaaccgagcacaagcacgttcaactcaggtaggc
```

Figure 2 (cont.)

```
       ccggccagcggggcggcgaggaggcgctcccaggttccggccctccctcggccccgcgccgca
       ++++++++++++++++++++++++++++++++++++++++++++++++++++++++++++++++        14,885
       ggccggtcgccccgccgctcctccgcgagggtccaaggccgggaggggagccggggcgcggcgt gagtctggccgcgcgcccctgcgcaacgtggcaggaagcgcgcgctgggggcggggacgggcagt
       ++++++++++++++++++++++++++++++++++++++++++++++++++++++++++++++++        14,950
       ctcagaccggcgcgcggggacgcgttgcaccgtccttcgcgcgcgaccccgccctgccgtca agggctgagcggctgcggggcgggtgcaagcacgtttccgacttgagttgcctcaagagggcgt
       ++++++++++++++++++++++++++++++++++++++++++++++++++++++++++++++++        15,015
       tcccgactcgccgacgccccgcccacgttcgtgcaaaggctgaactcaacggagttctccccgca gctgagccagacctccatcgcgcactccggggagtggagggaaggagcgagggctcagttgggct
       ++++++++++++++++++++++++++++++++++++++++++++++++++++++++++++++++        15,080
       cgactcggtctggaggtagcgcgtgaggcccctcacctcccttcctcgctcccgagtcaaccga gttttggaggcaggaagcacttgctctcccaaagtcgctctgagttgttatcagtaagggagctg
       ++++++++++++++++++++++++++++++++++++++++++++++++++++++++++++++++        15,145
       caaaacctccgtccttcgtgaacgagagggtttcagcgagactcaacaatagtcattccctcgac cagtggagtaggcggggagaaggccgcacccttctccggaggggggaggggagtgttgcaatacc
       ++++++++++++++++++++++++++++++++++++++++++++++++++++++++++++++++        15,210
       gtcacctcatccgcccctcttccggcgtgggaagaggcctccccctccctcacaacgttatgg PasI
                                                |
       tttctgggagttctctgctgcctcctggcttctgaggaccgccctgggcctgggagaatcccttg
       ++++++++++++++++++++++++++++++++++++++++++++++++++++++++++++++++        15,275
       aaagaccctcaagagacgacggaggaccgaagactcctggcgggacccggaccctcttagggaac cccctcttccctcgtgatctgcaactccagtctttcttaat      3'
       ++++++++++++++++++++++++++++++++++++++++   •••  15,318
       ggggagaaggggagcactagacgttgaggtcagaaagaatta     5'
```

MICE WITH TRANSGENE OF IBOX PEPTIDE INHIBITOR OF GROUP B P21-ACTIVATED KINASES

CROSS-REFERENCE TO RELATED APPLICATIONS

This application claims priority to U.S. Application No. 62/378,769, filed Aug. 24, 2016, which is incorporated herein by reference in its entirety.

REFERENCE TO GOVERNMENT GRANTS

This invention was made with government support under Grant Nos. CA142928 and CA148805 awarded by the National Institutes of Health. The government has certain rights in the invention.

FIELD

The present disclosure relates generally to the field of transgenic animals. More particularly, the present disclosure relates to transgenic mice comprising a peptide inhibitor of Group B p21-activated kinase (Pak), the iBox peptide, that is constitutively expressed, including tissue-specific expression. The present disclosure further relates to cells, tissues, and organs obtainable from such mice, and methods for producing such mice.

BACKGROUND

Various Pak knock-out mice have been made. These mice only remove single group A or group B Pak genes and, therefore, cannot serve as a model of inhibition of the full group of Paks. In addition, knock-out mice eliminate Pak's scaffold function in addition to eliminating its kinase function.

SUMMARY

The present disclosure provides a transgenic mouse comprising a transgene comprising a nucleic acid sequence encoding a peptide inhibitor of Group B p21-activated kinase (Pak), the iBox peptide, which may optionally be operably linked to glutathione S-transferase (GST) to facilitate detection of this inhibitor. The transgene may further encode a fluorescent marker such as eGFP. In some embodiments, the transgene is stably integrated into the mouse genome, for example, into a chromosome. In some embodiments, the iBox peptide is constitutively expressed in the transgenic mouse. The expression may be limited to a particular cell, tissue, or organ of interest. The cell, tissue, or organ of interest may include the skin, tongue, esophagus, stomach, intestine, colon, mesothelium, Schwann cells, brain, lung, heart, liver, pancreas, kidney, bladder, testes, thyroid, ovaries, skeletal muscle, bone, or other organ, cell, or tissue. In some embodiments, the organ of interest is the pancreas. Cells, tissues, or organs comprising the transgene may be isolated from the transgenic mouse. Thus, the present disclosure provides a transgenic mouse comprising a transgene encoding the iBox peptide inhibitor.

In some embodiments, the transgene comprises the nucleic acid sequence of SEQ ID NO:1 (gaagcagaggactggacggcagccctgct-gaacaggggccgcagtcggcagccctggtgctaggggataactgattg ctgat-ttagttcacaattggatggagttgcctgaatga). In some embodiments, the transgene comprises the nucleic acid sequence of SEQ ID NO:2 (atgtccctatactaggttattggaaaattaagggccttgtgcaacc-cactcgac acttaggaatatcagaagaaaaatatgaagagcatagtatgagcgc-gatgaaggtgataaatggcgaaacaaaaagatgaattgggatg gagtacccaat-caccttattatattgatggtgatgaaaattaacacagtctatggccatcatacgtt atatagctgacaagcacaacatgagg gtggagtccaaaagagcgtgcagaga-tacaatgcttgaaggagcggattggatattagatacggtgatcgagaattg-catatagtaaaga catgaaactctcaaagagattacttagcaagctacct-gaaatgctgaaaatgacgaagatcgatatgtcataaaacatatttaaatggtgatc atgtaacccatcctgacttcatgagtatgacgctcagatgagattatacatggacc-caatgtgcctggatgcgacccaaaattagatgatta aaaaacgtattgaagc-tatcccacaaattgataagtacttgaaatccagcaagtatatagcatggc-catgcagggctggcaagccacgtag gtggtggcgaccatcctccaaaatcggatctggaccgcgtg-gatccgaagcagaggactggacggcagccctgctgaacaggggccgc agtcggcagcccctggtgctaggggataactgttttgctgatttagttcacaattg-gatggagttgcctgaatga). In some embodiments, the transgene further comprises the nucleic acid sequence of SEQ ID NO:3 (atggt gagcaagggcgaggagctgacaccggggtggtgcc-catcctggtcgagctggacggcgacgtaaacggccacaagacagcgtgtcc ggcgagggcgagggcgatgccacctacggcaagctgaccctgaaga-catctgcaccaccggcaagctgcccgtgccctggcccaccc tcgtgac-caccctgacctacggcgtgcagtgcttcagccgctaccccgaccacat-gaagcagcacgacttcttcaagtccgccatgcccga aggctacgtccaggagcgcaccatcttcttcaaggacgacggcaactacaa-gacccgcgccgaggtgaagttcgagggcgacaccctg gtgaaccg-catcgagctgaagggcatcgacttcaaggaggacggcaa-catcctggggcacaagctggagtacaactacaacagccaca acgtctatatcatggccgacaagcagaagaacggcatcaaggtgaacttcaa-gatccgccacaacatcgaggacggcagcgtgcagctc gccgaccac-taccagcagaacacccccatcggcgacggccccgtgctgctgcccgacaac-cactacctgagcacccagtccgccctga gcaaagaccccaacgagaagcgcgatcacatggtcctgctg-gagttcgtgaccgccgccgggatcactctcggcatggacgagctgtac aagta). The transgene may be inserted at the ROSA26 locus.

In some embodiments, the iBox transgene is expressed in one or more organs in the mouse. In some embodiments, the one or more organs includes the pancreas. In some embodiments, the iBox transgene is expressed only in the pancreas.

The mouse may further comprise a transgene encoding a KRas oncogene, which KRas oncogene may be expressed only in the pancreas. Thus, the transgenic mouse may comprise the iBox transgene and a KRas oncogene transgene, both of which may be expressed in the pancreas of the mouse. The KRas oncogene may comprise one or more alterations and the KRas oncogene induces pancreatic cancer in the mouse.

The present disclosure provides methods for producing a mouse comprising a transgene encoding the iBox peptide inhibitor. In general, the methods comprise introducing a nucleic acid sequence encoding the iBox peptide inhibitor into a mouse egg, embryo, or embryonic stem cell, and transferring the mouse egg, embryo, or embryonic stem cell having the introduced nucleic acid sequence into a female mouse. In some embodiments, the transgene comprises the nucleic acid sequence of SEQ ID NO:1. In some embodiments, the transgene comprises the nucleic acid sequence of SEQ ID NO:2. In some embodiments, the transgene further comprises the nucleic acid sequence of SEQ ID NO:3. The methods may further comprise breeding the female mouse and selecting offspring comprising the nucleic acid sequence. The female mouse may be bred, for example, with a male Cre mouse. Upon breeding the female mouse with a male Cre mouse, the offspring may be selected according to their expression of the iBox peptide. The methods may further comprise breeding the selected offspring, for example, with a second (male or female) Cre mouse comprising a transgene encoding a KRas oncogene. In some embodiments, the second Cre mouse expresses the KRas oncogene in the pancreas. Mice produced according to the inventive methods are also included.

BRIEF DESCRIPTION OF THE DRAWINGS

FIG. 2 shows the nucleic acid sequence of the pROSA26-Gst-iBox plasmid (circular plasmid, at 15,318 bp). Relevant sub-sections of the plasmid are designated.

FIG. 5A: mouse embryo fibroblasts (MEFs) derived from Tg-LSL-iBox mice were infected with an empty Adenovirus or Adenovirus-Cre. An anti-Gst blot is shown; FIG. 5B: proliferation rates of MEFs expressing iBox (Cre+); FIG. 5C: Pak4 was immunoprecipitated from lysates from these MEFs were assayed for Pak4 kinase activity; and FIG. 5D: lysates were probed for the indicated signaling molecules.

DESCRIPTION OF EMBODIMENTS

Figure 1:
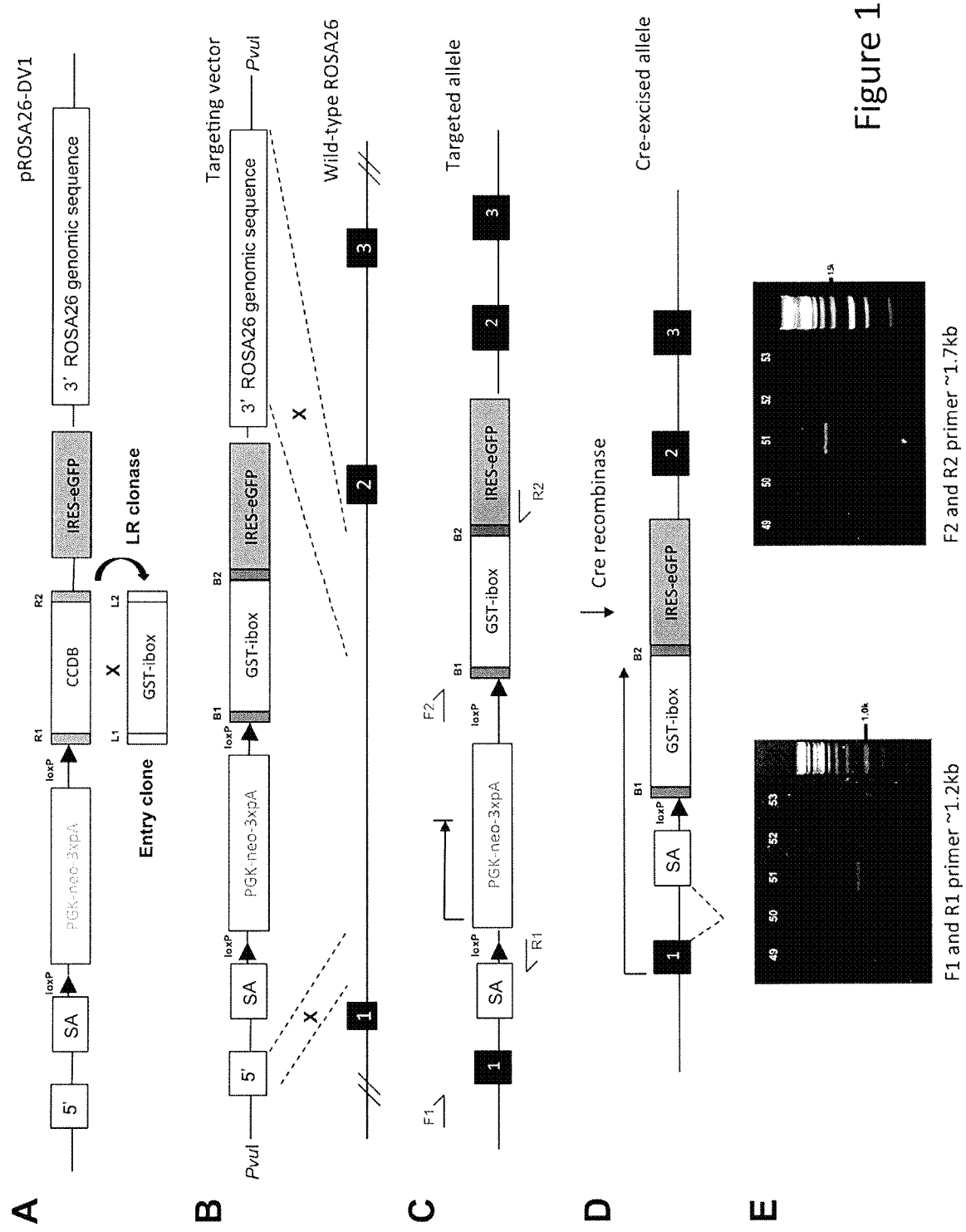
FIG. 1, panels A through E, show construction of an LSL-iBox knock-in vector and expected genomic organization in the mouse genome. Panel A shows an LR reaction performed between the pROSA26-DV1 vector and pEntry clone containing GST-iBox fragment to generate ROSA26 targeting vector. Panel B shows that homologous recombination occurred between exon 1 and 2 of wild-type ROSA26 locus in G4 ES cells after electroporation. Black boxes represent the exons located at ROSA26 locus. Panel C shows the genomic structure of the targeted allele. Panel D shows that the Cre-mediated deletion of intervening loxP flanked PGK-neo-3xpA (STOP) cassette results in the ROSA26-locus-based expression of an exonl-GST-iBox-IRES-eGFP bi-cistronic fusion transcript. Panel E shows genotyping PCR analysis of genomic DNA isolated from the tail detecting presence of fusion transcript by both external primers (F1 and R1) and internal primers (F2 and R2), verifying genomic organization of the LSL-iBox transgene.

Various terms relating to embodiments of the present disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, "Cre mouse" is a mouse that comprises a transgene encoding Cre recombinase (plural, "Cre mice"). The transgene may be expressed in one or more tissues or organs in the Cre mouse.

In order to determine the effects of inhibiting the Group B p21-activated kinases (Paks) in vivo, a vector was designed to overexpress a peptide inhibitor of Group B Paks (Pak 4, Pak 5, and Pak 6) in mice. This peptide inhibitor, termed iBox, is derived from amino acids 166 to 203 of the human INKA-1 protein. The iBox peptide transgene was linked to GST to facilitate detection upon expression. Transgene expression was restricted to a limited number of tissues in order to avoid the potential for wide-ranging, deleterious effects on development.

This transgenic mouse model is designed such that mice constitutively express the iBox peptide. In some embodiments, the transgene is compatible with the Cre-recombinase system. Thus, for example, when a mouse comprising the iBox transgene is bred with a particular Cre recombinase-expressing mouse, the iBox peptide is expressed in the offspring. As there are many Cre-recombinase mice available, including mice with Cre-recombinase expression limited to particular tissues, it is possible to have tissue-specific expression of the iBox peptide. Accordingly, Group B Pak inhibition can be tissue specific. Tissue specificity may be useful, for example, in evaluating the role of Group B Paks in mouse development, tissue development, organ development, organ function, and system cross-talk. Tissue specificity may also be useful in evaluating disease, including cancer, diseases in which Group B Pak activity or impaired or inhibited activity is implicated, and other conditions that relate, directly or indirectly, to Group B Pak activity or impaired or inhibited activity.

The transgenic mice allow the evaluation of the role of group B Paks in preclinical cancer models. Group B Paks may be conditionally inhibited in mice in any tissue at any time. This allows an assessment concerning the loss of Group B Pak activity, e.g., whether the loss may be beneficial in any condition, such as cancer. Unlike Pak-knock-out mice, the iBox transgenic mouse continues to express endogenous group B Pak proteins, such that the expression of the iBox transgene will mimic the effects of a small molecule group B Pak inhibitor, thereby predicting drug effects on Pak 3, 4, and/or 5 inhibition. Thus, by expressing a regulated peptide inhibitor of Group B Paks, the iBox transgenic mouse model provides a better indicator of small molecule inhibitors than knock-outs or shRNA-expressing mice, as endogenous Pak proteins are still expressed.

For example, it is believed that Group B Pak inhibition may be relevant to pancreatic cancer treatment. Accordingly, a model of Group B Pak inhibition in the pancreas may establish any one or combination of the Group B Paks as a druggable target. The survival of transgenic mice with the iBox peptide expressed in the pancreas is compared to control mice in which the iBox peptide is not expressed in the pancreas, or in which the iBox peptide is expressed in other tissue (aside from the pancreas).

It is believed that the iBox inhibitor is specific to Group B Paks (e.g., Pak 4, 5, and 6), and does not titrate out other binding partners, such as small GTPases, PIX, or Nck. As well, expression of the iBox peptide is regulated by Cre recombinase in the mouse, thereby allowing flexibility in Pak inhibition in particular tissues and at particular times. An additional advantage is that the iBox inhibitor transgene is inserted as a single copy into a safe, well-characterized location in the genome (the ROSA26 locus), thus not disturbing expression of other mouse genes that may be key to continued viability of the mouse from conception through adulthood. FIG. 1, panels A through E, describes an exemplary embodiment of the generation of the ROSA26-promoter-based expression of the iBox transgene. The ROSA26-promoter was selected for gene expression because it is known as a safe harbor site in the mouse genome, whereby insertion of the iBox transgene was not expected to not disrupt the expression of other genes of the mouse.

Generally, a gateway enzyme mix (LR-clonase) is used to catalyze recombination between an entry clone (containing a gene of interest flanked by attL sites) and a destination vector (containing attR sites) to generate an expression clone. More specifically, the LR-clonase reaction can be used to insert the pROSA26-DV1 vector and pEntry clone containing GST-iBox (GST as reporter) fragment to generate ROSA26 targeting vector as shown in Panel B. Using this technique, homologous recombination occurred between exon 1 and 2 of wild-type ROSA26 locus in G4 ES cells after electroporation as shown in Panel B. The targeted allele comprises a fused GST-iBox gene sequence, as well as the reporter gene sequence, IRES-eGFP, as shown in Panel C.

During recombination, a Cre recombinase-mediated deletion of intervening loxP flanked PGK-neo-3xpA (STOP) cassette occurs in the ROSA26-locus-based expression of an exonl-GST-iBox-IRES-eGFP bi-cistronic fusion transcript. This deletion results from Cre-Lox recombinase technology at a site-specific location so that the GST-iBox gene sequence can be expressed. The system consists of a single enzyme, Cre recombinase, that recombines a pair of short target sequences, e.g., the Lox sequences, without the need to insert extra supporting proteins or sequences. Placing the Lox sequence appropriately flanking the PGK-neo-3xpA (STOP) cassette allows the genes to be deleted. As a result, the activity of the Cre recombinase enzyme can be controlled so that it is expressed in a particular cell type or triggered by an external stimulus like a chemical signal or a heat shock. These targeted DNA changes are useful in cell lineage tracing and when mutants are lethal if expressed globally.

Genotyping using PCR analysis of genomic DNA isolated from tail detecting presence of fusion transcript by both external primers (F1 and R1) and internal primers (F2 and R2). These primers are as follows:

```
                                              (SEQ ID NO: 4)
    F1:  5'-TAGGTAGGGGATCGGGACTCT-3';

(SEQ ID NO: 5)
    R1:  5'-GCGAAGAGTTTGTCCTCAACC-3';

(SEQ ID NO: 6)
    F2:  5'-CCCATCAAGCTGATCCGGAAC-3';
    and (SEQ ID NO: 7)
    R2:  5'-GTGAACAGCTCCTCGCCCTTG-3'.
```

These primers were used to confirm expression of the GST-iBox gene sequence in vitro and in vivo. The IRES-eGFP plasmid was used to confirm expression of GST-iBox plasmid. Viable GST-iBox transgenic mice can be produced, and these mice allow constitutive expression of a potent peptide inhibitor of Group B Paks (Pak 3, Pak 4, and Pak 5), iBox. In preliminary experiments, the expression of the iBox transgene inhibited cell proliferation in each of the tissues studied. The iBox gene sequence is provided as SEQ ID NO:1, the GST-iBox gene sequence is shown in SEQ ID NO:2. The GST-iBox plasmid sequence is shown in FIG. 2.

The present disclosure provides iBox transgenic mice. This provides control of expression of the transgene in mice, and they may be useful as a tool to aid studies of development, tissue renewal, aging, cancer, and a variety of conditions or diseases that involve cell proliferation.

Figure 3:
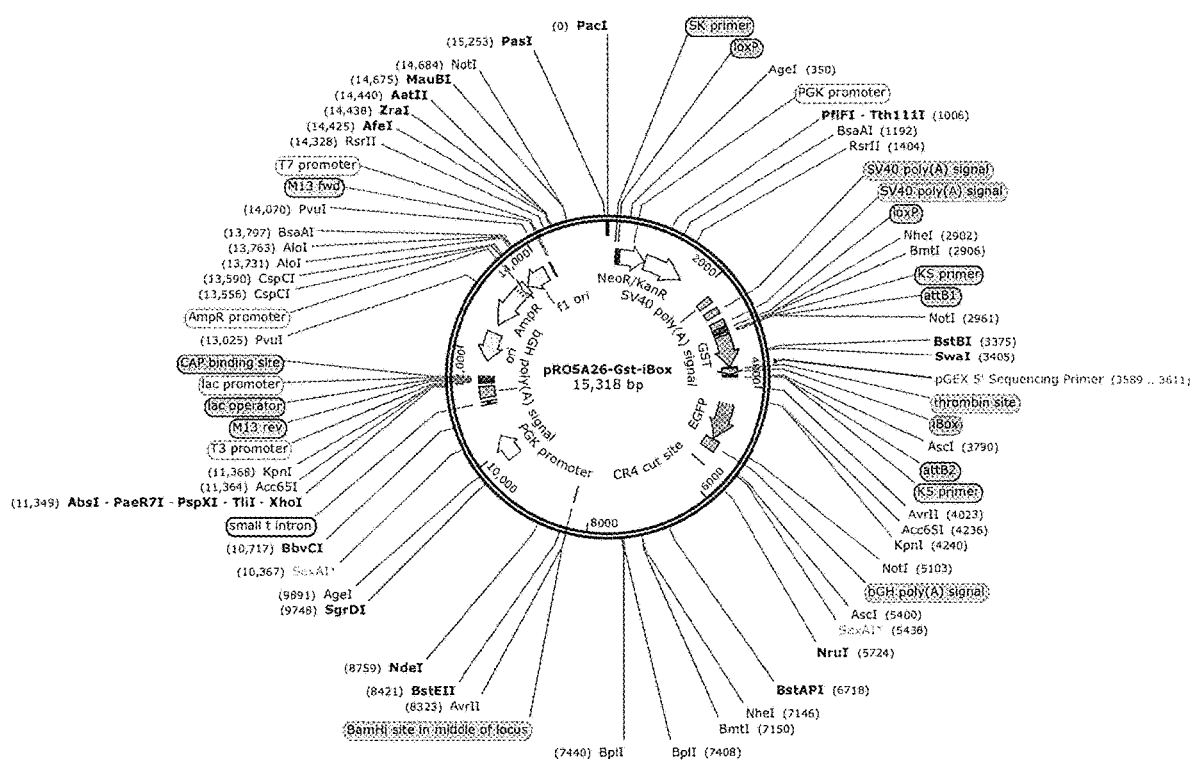
FIG. 3 shows a map of the pROSA26-Gst-iBox plasmid.

In one aspect, a transgenic mouse comprises a transgene comprising a nucleic acid sequence encoding a peptide inhibitor of Group B Paks (Pak 4, Pak 5, and Pak 6), iBox. In some embodiments, the mouse comprises a transgene comprising a nucleic acid sequence encoding the iBox peptide linked to GST. The mice comprise at least one copy of the transgene which, in some embodiments, is stably integrated into a chromosome. The transgene may be present in the gametes and/or somatic cells of the animal. The transgene may comprise the nucleic acid sequence of SEQ ID NO:1 or SEQ ID NO:2 or the complement thereof. The transgene may further comprise the nucleic acid sequence of SEQ ID NO:3 (eGFP). The iBox plasmid for transformation may comprise the plasmid shown in FIG. 2 and FIG. 3.

In some embodiments, the transgene is present in and capable of expression in one or more tissues or organs in the mouse. Exemplary tissues and organs include, but are not limited to, the skin, tongue, bone marrow, brain, heart, liver, kidney, lung, pancreas, bladder, mammary tissue, skeletal muscle, esophagus, stomach, small intestine, and large intestine, or any subpart thereof. Cells, tissues, or organs comprising the transgene may be isolated from the mouse, and may be grown in culture and/or subjected to further study. Cells, tissue, or organs comprising the iBox transgene (e.g., SEQ ID NO:1 or SEQ ID NO:2) isolated or obtained from a mouse further are provided.

Figure 4:
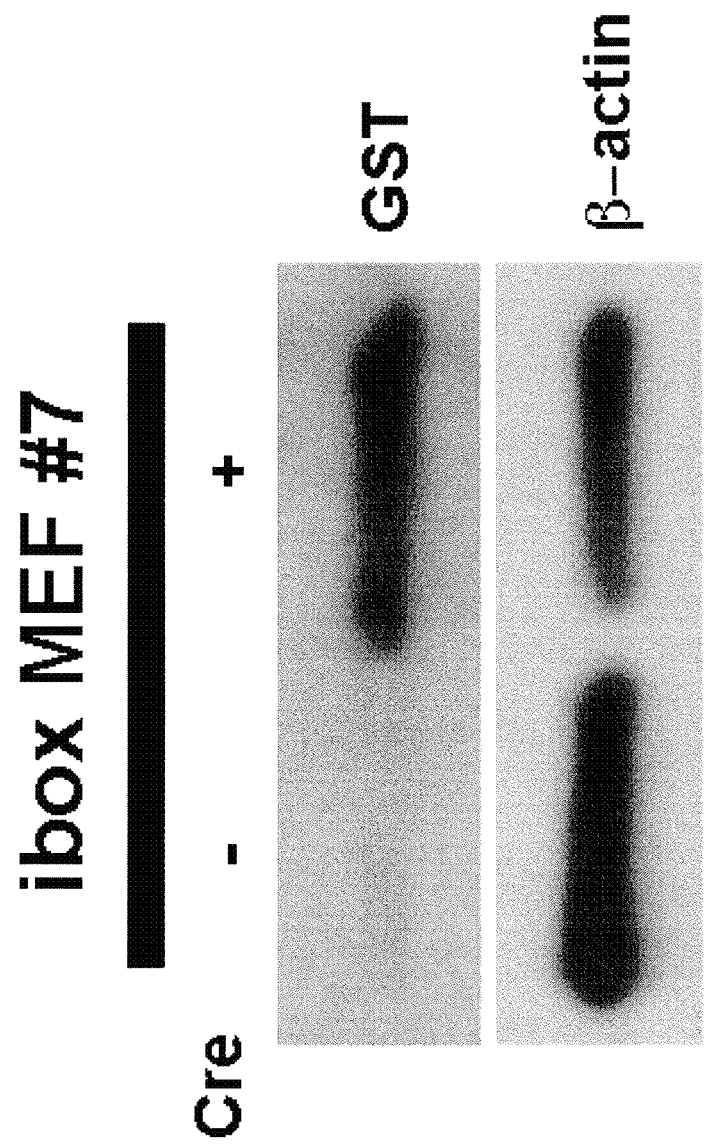
FIG. 4 shows the expression of Gst-iBox in cells from transgenic mice. Mouse embryonic fibroblasts (MEFs) were established from an e13 embryo from a transgenic mouse (#7). These MEFs were transduced with an adenovirus encoding no insert (−) or the Cre gene (+) to remove the LSL cassette and permit Gst-iBox expression. 2 days post adenoviral infection, cell lysates were analyzed by immunoblot with anti-Gst antibodies.

It is possible to achieve tissue-specific (and organ-specific) expression of the iBox transgene, for example, by breeding the foxed iBox mouse with a Cre mouse having the Cre recombinase gene expressed in particular tissues or organs. An example of expression of the iBox transgene following Cre-mediated excision of the LSL motif is shown in FIG. 4. For example, a Cre mouse can include, but not be limited to, CDX2-Cre, Tie2-Cre, Postn-Cre, B6.FVB-Tg (Pdx1-cre)6Tuv/J (Pdx-Cre), in addition to others. Many Cre mice are commercially available, including many mice with particular tissues having Cre. Any such Cre mice are suitable for breeding with the foxed iBox mouse in order to establish tissue-specific expression of the iBox transgene. Cre mice are available, for example, from The Jackson Laboratory (world wide web at jax.org). Constitutive expression of the transgene in particular tissues can thus be achieved through breeding with appropriate Cre mice.

The Group B Paks (Pak 4, 5, and 6) may be expressed in any combination in a given tissue. Some tissues within the body express all three Group B Paks, though other tissues in the body express only one or two of these Group B Paks. As well, some tissues in the body may express more of a particular Group B Pak or combination thereof than another Group B Pak. Thus, for example, in embodiments where a given organ or tissue expresses only a single Group B Pak, the effects of the iBox inhibitor and, more generally, on inhibition of that Group B Pak can be assessed.

The present disclosure is not limited to mice, and can include any member of a category of other non-human mammals such as rodents (e.g., rats, rabbits), companion animals, farm animals, non-human primates, and other non-human mammals. Any non-human animal expressing Cre, which can be bred with any non-human animal expressing a foxed iBox transgene, can produce iBox transgene expression. Mice, being exemplified, are suitable.

The present disclosure also provides methods for producing a transgenic mouse, as well as mice produced by any of the methods. In some embodiments, the method comprises breeding a mouse comprising an iBox transgene (e.g., foxed iBox) with a Cre mouse, and selecting offspring having the iBox transgene and the CRE-expressing transgene. Such offspring should express the iBox peptide.

In some embodiments, the method comprises introducing a nucleic acid sequence encoding the iBox peptide inhibitor into a mouse egg (fertilized or unfertilized), zygote, embryo, or embryonic stem cell, and transferring the mouse egg, zygote, embryo, or embryonic stem cell having the introduced nucleic acid sequence into a female mouse. The method may further comprise fertilizing the egg. The method may further comprise breeding the female mouse and selecting offspring having the nucleic acid sequence. Offspring may be referred to as "progeny."

In some embodiments, the method comprises introducing a nucleic acid sequence encoding iBox peptide inhibitor into a mouse egg (fertilized or unfertilized), zygote, embryo, or embryonic stem cell, transferring the mouse egg, zygote, embryo, or embryonic stem cell having the introduced nucleic acid sequence into a female mouse, breeding the female mouse with a male Cre mouse, and selecting offspring having the nucleic acid sequence and the CRE-expressing transgene, expressed in specific target tissues. Such offspring should express the iBox peptide in the target tissues.

Any technique suitable for introducing the nucleic acid sequence may be used. Non-limiting examples include electroporation, microinjection, viruses, lipofection, calcium phosphate, and other known transformation techniques.

Animals, including offspring, may be screened to confirm the presence of the transgene according to any technique suitable in the art. For example, cells may be isolated and tested for the presence of the gene, a detectable marker, selection marker, translation product, detectable mRNA, and/or detectable phenotype. Green fluorescent protein (GFP) or enhanced GFP (eGFP), or similar fluorescent marker, may be linked to or co-expressed with the iBox transgene to confirm presence, as well as expression of the transgene. The eGFP protein may comprise the protein encoded by the nucleic acid sequence of SEQ ID NO:3.

Offspring carrying the transgene can further be bred with other animals to perpetuate the transgenic line, or can be bred with animals carrying other transgenes. Breeding includes back crossing, including back crossing into distinct genetic backgrounds. Offspring include any filial or back-cross generation.

In some embodiments, offspring from the iBox+Cre mice (e.g., mice expressing the iBox transgene) can be further bred with a Cre-induced cancer model mouse. For example, mice with a mutant KRAS transgene under loxP control can be bred with a Cre mouse comprising Cre in the pancreas, creating pancreas-specific expression of the mutant KRAS gene to induce mutant KRAS expression in the pancreas of progeny mice. The progeny mice will therefore develop pancreatic cancer. Such mutant-KRAS-expressing progeny mice can then be further bred with an iBox-expressing mouse, to determine the effect of Group B Pak inhibition (via the expressed iBox peptide) on KRAS-induced pancreatic cancer.

The following representative embodiments are presented:

Embodiment 1

A transgenic mouse, comprising a transgene encoding the iBox peptide inhibitor.

Embodiment 2

The transgenic mouse according to embodiment 1, wherein the transgene comprises the nucleic acid sequence of SEQ ID NO:1.

Embodiment 3

The transgenic mouse according to embodiment 1 or 2, wherein the transgene comprises the nucleic acid sequence of SEQ ID NO:2.

Embodiment 4

The transgenic mouse according to any one of embodiments 1 to 3, wherein the transgene further comprises the nucleic acid sequence of SEQ ID NO:3.

Embodiment 5

The transgenic mouse according to any one of embodiments 1 to 4, wherein the transgene is inserted at the ROSA26 locus.

Embodiment 6

The transgenic mouse according to any one of embodiments 1 to 5, wherein the transgene is expressed in a single organ in the mouse.

Embodiment 7

The transgenic mouse according to embodiment 6, wherein the organ is the pancreas.

Embodiment 8

The transgenic mouse according to embodiment 7, wherein the mouse further comprises a transgene encoding a KRas oncogene in the pancreas.

Embodiment 9

The transgenic mouse according to embodiment 8, wherein the KRas oncogene comprises one or more alterations.

Embodiment 10

A cell isolated from the transgenic mouse according to any one of embodiments 1 to 9, wherein the cell comprises the transgene.

Embodiment 11

A tissue isolated from the transgenic mouse according to any one of embodiments 1 to 9, wherein at least one cell in the tissue comprises the transgene.

Embodiment 12

An organ isolated from the transgenic mouse according to any one of embodiments 1 to 9, wherein at least one cell in the organ comprises the transgene.

Embodiment 13

The organ according to embodiment 12, wherein the organ is the pancreas.

Embodiment 14

A method for producing a mouse comprising a transgene encoding the iBox peptide inhibitor, comprising introducing a nucleic acid sequence encoding the iBox peptide inhibitor into a mouse egg, embryo, or embryonic stem cell, and transferring the mouse egg, embryo, or embryonic stem cell having the introduced nucleic acid sequence into a female mouse.

Embodiment 15

The method according to embodiment 14, wherein the nucleic acid sequence comprises the nucleic acid sequence of SEQ ID NO:1.

Embodiment 16

The method according to embodiment 14 or 15, wherein the nucleic acid sequence comprises the nucleic acid sequence of SEQ ID NO:2.

Embodiment 17

The method according to any one of embodiments 14 to 16, wherein the nucleic acid sequence further comprises the nucleic acid sequence of SEQ ID NO:3.

Embodiment 18

The method according to any one of embodiments 14 to 17, further comprising breeding the female mouse and selecting offspring having the nucleic acid sequence.

Embodiment 19

A mouse produced according to the methods of any one of embodiments 14 to 18.

Embodiment 20

A method for producing a mouse comprising a transgene encoding the iBox peptide inhibitor, comprising introducing a nucleic acid sequence encoding the iBox peptide inhibitor into a mouse egg, embryo, or embryonic stem cell, and transferring the mouse egg, embryo, or embryonic stem cell having the introduced nucleic acid sequence into a female mouse, breeding the female mouse with a male Cre mouse, and selecting offspring expressing the iBox transgene.

Embodiment 21

The method according to embodiment 20, wherein the nucleic acid sequence comprises the nucleic acid sequence of SEQ ID NO:1.

Embodiment 22

The method according to embodiment 20 or 21, wherein the nucleic acid sequence comprises the nucleic acid sequence of SEQ ID NO:2.

Embodiment 23

The method according to any one of embodiments 20 to 22, wherein the nucleic acid sequence further comprises the nucleic acid sequence of SEQ ID NO:3.

Embodiment 24

The method according to any one of embodiments 20 to 23, wherein the male Cre mouse expresses Cre recombinase in a single organ.

Embodiment 25

The method according to embodiment 24, wherein the single organ is the pancreas.

Embodiment 26

The method according to any one of embodiments 20 to 25, further comprising breeding the offspring with a second Cre mouse comprising a transgene encoding a KRas oncogene.

Embodiment 27

The method according to embodiment 26, wherein the second Cre mouse expresses the KRas oncogene in the pancreas.

Embodiment 28

The method according to embodiment 26 or 27, wherein the KRas oncogene comprises one or more alterations.

Embodiment 29

A mouse produced according to the methods of any one of embodiments 20 to 28.

The following examples are provided to describe the present disclosure in greater detail. They are intended to illustrate, not to limit, the present disclosure.

EXAMPLES

Example 1: General Experimental Methods

Gateway-Compatible Vector Construction

The Gateway-compatible pROSA26-DV1 was obtained from Dr. Jody Haigh. A GST-iBox fragment was cloned into a pEntry vector after PCR and gel purification. The LR reaction was performed using Clonase™ Enzyme Mix (Life Technology) according to the manufacture's instruction. A positive clone (pROSA26-GST-iBox-IRES-eGFP) was analyzed by restriction digests and sequencing. In particular, pROSA26-GST-iBox-IRES-eGFP was linearized by PvuI and electroporated into G4 ES cells.

Generation of Transgenic Mice

B6C3F1 female mice were superovulated with 5 iu of PMSG and 5 iu of hCG each, and mated to B6C3F1 males to generate 1-cell fertilized embryos for microinjection. ROSA26 L/R zinc finger nuclease mRNA (50 ng/µl) and iBox DNA construct (2 ng/µl) were injected into the embryos' pronuclei. The surviving embryos were implanted into d0.5 pseudo-pregnant recipient mothers (Swiss Webster).

The pROSA26-GST-iBox-IRES-eGFP plasmid was co-injected with Zinc-finger constructs targeting the Rosa26 locus into mouse zygotes. Zygotes were obtained by super-ovulation of C57BL/6N females (Charles River). The next day zygotes were collected from oviducts and microinjected in M2 embryo medium following standard procedures with a mixture of targeting vector and ZFNRosa mRNAs (2.5 ng/µL each) loaded into a single microinjection needle. For microinjection a two-step procedure was applied: A first aliquot of the DNA/RNA mixture was injected into the male pronucleus (to deliver the DNA vector, as used for the production of transgenic mice). Upon the withdrawal of the injection needle from the pronucleus, a second aliquot of the DNA/RNA mixture was injected into the cytoplasm to deliver the ZFN mRNA directly to the translation machinery. Injections were performed using a Leica micromanipulator and microscope and an Eppendorf FemtoJet injection device. Injected zygotes were transferred into pseudopregnant CD1 female mice and fetuses recovered at day E18 for further analysis. Recovered fetuses were analyzed by PCR using the F1 and R1, and F2 and R2 primers to identify successfully targeted mice. Genomic DNA of pups was prepared from tails for detecting existence of transgene by both external primer (F1 and R1) and internal primer (F2 and R2).

Cell Culture, Transfections and Infections

Primary mouse embryo fibroblasts were established from E14 embryos from pregnant ROSA26-iBox mice. Cell lines were maintained in DMEM medium supplemented with 10% of FBS, 2 mM L-glutamine and 100 Um' penicillin/streptomycin ay 37° C. in a humidified 5% $CO_2$ incubator. To document iBox and EGFP expression, the MEFs were transduced with Adeno-Cre which removes the LSL cassette. MEFs were imaged to documents EGFP expression and lysates were probed by immunoblot to document iBox expression using anti-GST antibodies that recognize the GST protein that is fused to the N-terminus of iBox. These lysates were also probed with antibodies against Erk and P-Erk, Src and P-Src, Fak and P-Fak, as well as GAPDH.

Cell Proliferation Assay

Figure 5B:
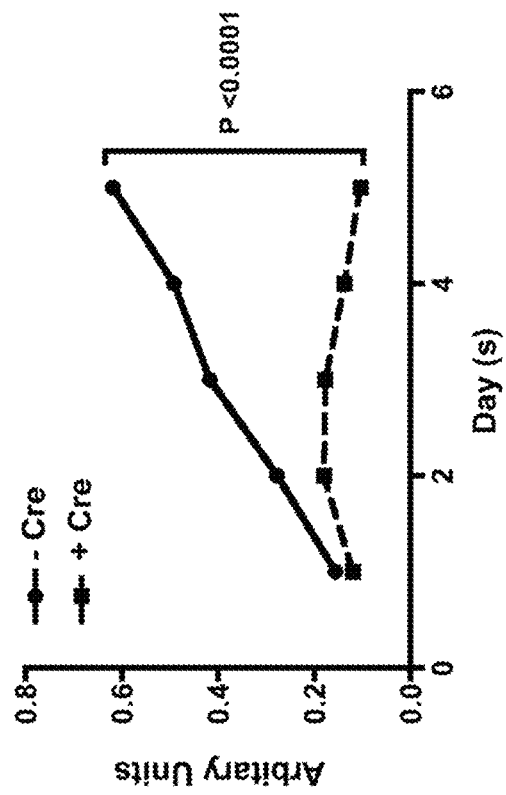
FIGS. 5A-5D show the expression of iBox and its effects on signaling.
Figure 5A:
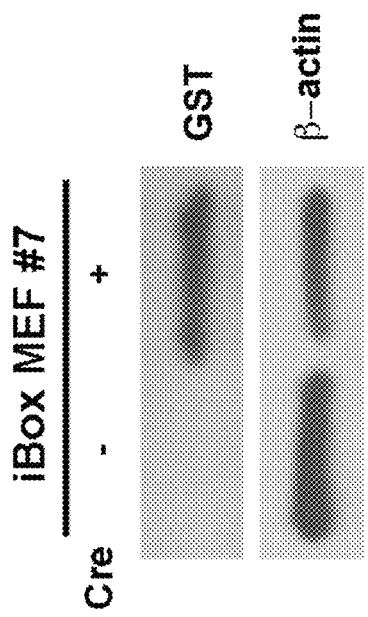

Cells were plated at $2 \times 10^3$ in 96-well plates and 10 µl of 3-[4,5-dimethylthiazol-2-yl]-2,5-diphenyl tetrazolium bromide (MTT) solution was added to each well to a final concentration of 0.5 mg/ml. The reaction was stopped after 4 hours at 37° C. by adding 100 µl of solubilization solution (10% SDS in 0.01M HCl) and the samples were analyzed at 595 nm on Perkin Elmer Envision plate reader. Triplicates were performed for each sample, and experiments were performed on three occasions. FIG. 5A shows mouse embryo fibroblasts (MEFs) derived from Tg-LSL-iBox mice were infected with an empty Adenovirus or Adenovirus-Cre. An anti-Gst blot is shown. FIG. 5B shows proliferation rates of MEFs expressing iBox (Cre+).

Kinase Assay

Figures 5C, 5D:
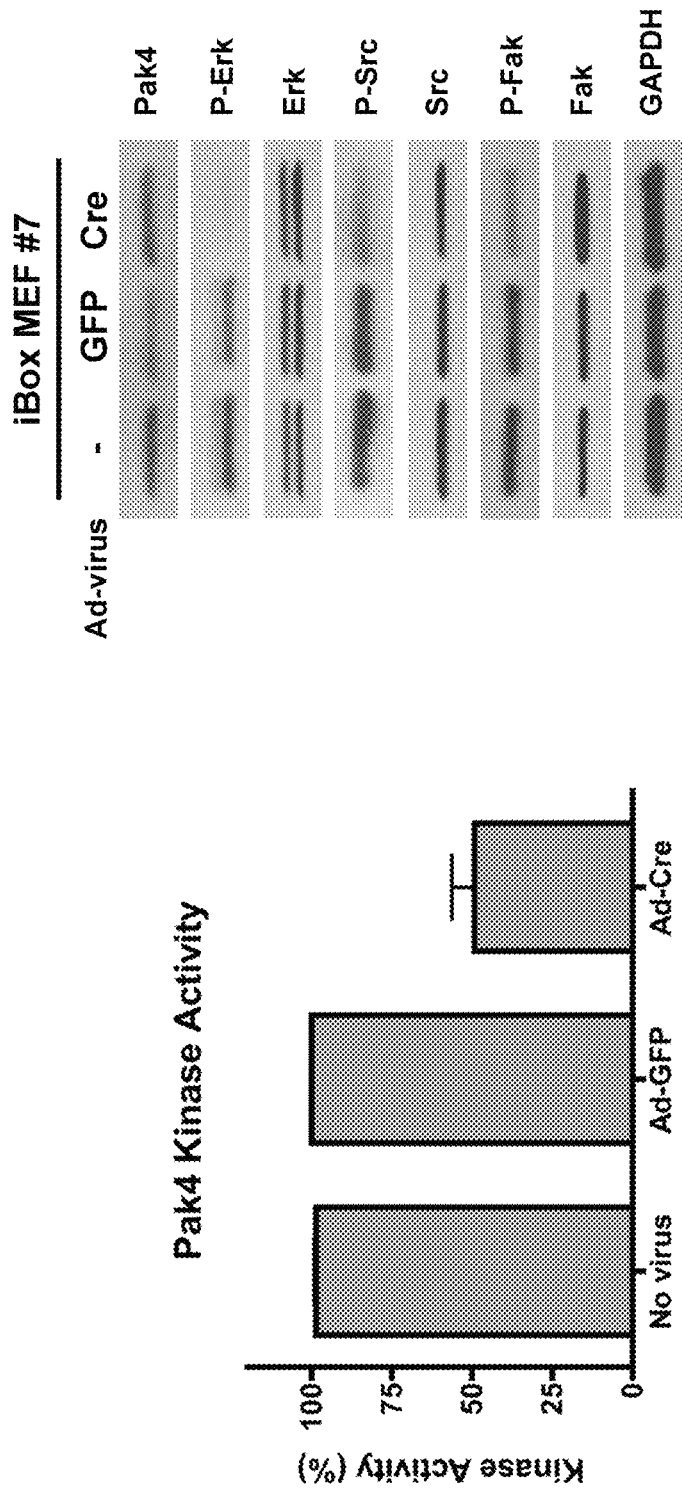

To analyze endogenous Pak4 activity, Pak4 was immunoprecipitated from ROSA26-iBox MEFs and Protein-A-Pak4 beads were incubated with recombinant Pacsin or CRTC1 for 10 minutes at 30° C. in a buffer containing 50 mM Tris-HCl, pH 7.5, 10 mM $MgCl_2$, 1 mM DTT, and 50 µM ATP. Reactions were terminated with hot 6×SDS/PAGE buffer and the samples were analyzed by immunoblot using anti-P-pacsin or anti-P-CRTC1 antibodies. FIG. 5C shows Pak4 was immunoprecipitated from lysates from these MEFs were assayed for Pak4 kinase activity. FIG. 5D shows lysates were probed for the indicated signaling molecules. Inhibition of Erk, Src, and Fak was observed.

The present disclosure is not limited to the embodiments described and exemplified above, but is capable of variation and modification within the scope of the appended claims.

What is claimed is:

1. A transgenic mouse whose genome comprises a transgene in an endogenous ROSA26 gene, wherein the transgene comprises:
   i) a nucleic acid sequence encoding an iBox peptide having the nucleic acid sequence of SEQ ID NO: 1 or SEQ ID NO: 2; and
   ii) a stop cassette flanked by recombination target sites, wherein the stop cassette comprises a nucleic acid sequence encoding a positive selection marker operably linked to a constitutive promoter and at least three polyadenylation signal sequences,
   wherein: the positive selection marker is functionally expressed in the mouse under the control of the constitutive promoter,
   the stop cassette prevents expression of the iBox peptide in the mouse, and
   recombination of the transgene is capable of deleting the stop cassette and allowing functional expression of the iBox peptide under the control of the endogenous ROSA26 promoter.

2. The transgenic mouse of claim 1, wherein the transgene has the nucleic acid sequence of SEQ ID NO: 3.

3. A transgenic mouse obtained by crossing the mouse of claim 1 with a transgenic mouse that expresses recombinase specifically in the pancreas, wherein the mouse obtained displays pancreas-specific expression of the iBox but not the positive selectable marker.

4. A transgenic mouse obtained by crossing the mouse of claim 1 with a transgenic mouse whose genome comprises a nucleic acid sequence encoding recombinase operably linked to a pancreas-specific promoter and a nucleic acid sequence encoding KRAS flanked by loxP sites that displays pancreas-specific expression of KRAS, wherein the mouse obtained displays pancreas-specific expression of the iBox and KRAS but not the positive selectable marker.

5. A method of making a transgenic mouse, the method comprising:
   a) introducing a nucleic acid sequence into an endogenous ROSA26 gene into an isolated mouse egg, embryo, or embryonic stem (ES) cell, wherein the nucleic acid sequence comprises:
      i) a nucleic acid sequence encoding an iBox peptide having the nucleic acid sequence of SEQ ID NO: 1 or SEQ ID NO: 2; and
      ii) a stop cassette flanked by recombination target sites and is positioned between an endogenous ROSA26 promoter comprising a nucleic acid sequence encoding a positive selection marker operably linked to a constitutive promoter and at least three polyadenylation signal sequences, wherein the stop cassette is located between an endogenous ROSA26 promoter and the nucleic acid sequence encoding the iBox peptide
      wherein: the positive selection marker is functionally expressed in the mouse, expression of the positive selection marker prevents expression of the iBox peptide in the mouse, and recombination of the transgene is capable of deleting the stop cassette and allowing functional expression of the iBox peptide under the control of the endogenous ROSA26 promoter;
   b) fertilizing the egg obtained in step a), and implanting the fertilized egg into a recipient female;
   transferring the embryo obtained in step a) into a recipient female; or
   injecting the ES cell obtained in step a) into an embryo in a recipient female;
   c) obtaining the transgenic mouse of claim 1 from the recipient female.

6. The method of claim 5, wherein the nucleic acid sequence introduced has the nucleic acid sequence of SEQ ID NO: 3.

7. A method of making a transgenic mouse, the method comprising:
   a) crossing a transgenic mouse obtained by the method of claim 5 with a transgenic mouse whose genome comprises a nucleic acid sequence encoding recombinase operably linked to a pancreas-specific promoter,
   such that a transgenic mouse that displays pancreas-specific expression of the iBox but not the positive selectable marker is obtained.

8. The method of claim 5, wherein the nucleic acid sequence introduced has the nucleic acid sequence of SEQ ID NO: 3.

9. A method of making a transgenic mouse model of pancreatic cancer, the method comprising:
   a) crossing a transgenic mouse obtained by the method of claim 5 with a transgenic mouse whose genome comprises a nucleic acid sequence encoding recombinase operably linked to a pancreas-specific promoter and a nucleic acid sequence encoding KRAS flanked by loxP sites,
   such that a transgenic mouse that displays pancreas-specific expression of the iBox and KRAS but not the positive selectable marker is obtained.

* * * * *

SEQUENCE LISTING

```
<160> NUMBER OF SEQ ID NOS: 7

<210> SEQ ID NO 1
<211> LENGTH: 117
<212> TYPE: DNA
<213> ORGANISM: Artificial sequence
<220> FEATURE:
<223> OTHER INFORMATION: transgene nucleic acid sequence

<400> SEQUENCE: 1
gaagcagagg actggacggc agccctgctg aacaggggcc gcagtcggca gccctggtg      60 ctagggata actgttttgc tgatttagtt cacaattgga tggagttgcc tgaatga       117

<210> SEQ ID NO 2
<211> LENGTH: 795
<212> TYPE: DNA
<213> ORGANISM: Artificial sequence
<220> FEATURE:
<223> OTHER INFORMATION: transgene nucleic acid sequence

<400> SEQUENCE: 2 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240 atgtgggtg gttgtccaaa agagcgtgca gagatttcaa tgcttgaagg agcggttttg    300 gatattgat acgtgtttc gagaattgca tatagtaaag actttgaaac tctcaaagtt     360
gattttctta gcaagctacc tgaaatgctg aaaatgttcg aagatcgttt atgtcataaa    420
```

| | | |
|---|---|---|
| acatatttaa atggtgatca tgtaacccat cctgacttca tgttgtatga cgctcttgat | | 480 |
| gttgttttat acatggaccc aatgtgcctg gatgcgttcc caaaattagt ttgttttaaa | | 540 |
| aaacgtattg aagctatccc acaaattgat aagtacttga atccagcaa gtatatagca | | 600 |
| tggcctttgc agggctggca agccacgttt ggtggtggcg accatcctcc aaaatcggat | | 660 |
| ctggttccgc gtggatccga agcagaggac tggacggcag ccctgctgaa caggggccgc | | 720 |
| agtcggcagc ccctggtgct aggggataac tgttttgctg atttagttca caattggatg | | 780 |
| gagttgcctg aatga | | 795 |

<210> SEQ ID NO 3
<211> LENGTH: 719
<212> TYPE: DNA
<213> ORGANISM: Artificial sequence
<220> FEATURE:
<223> OTHER INFORMATION: transgene nucleic acid sequence

<400> SEQUENCE: 3

| | | |
|---|---|---|
| atggtgagca agggcgagga gctgttcacc ggggtggtgc ccatcctggt cgagctggac | | 60 |
| ggcgacgtaa acggccacaa gttcagcgtg tccggcgagg gcgagggcga tgccacctac | | 120 |
| ggcaagctga ccctgaagtt catctgcacc accggcaagc tgcccgtgcc ctggcccacc | | 180 |
| ctcgtgacca cccctgaccta cggcgtgcag tgcttcagcc gctacccga ccacatgaag | | 240 |
| cagcacgact tcttcaagtc cgccatgccc gaaggctacg tccaggagcg caccatcttc | | 300 |
| ttcaaggacg acggcaacta caagacccgc gccgaggtga agttcgaggg cgacaccctg | | 360 |
| gtgaaccgca tcgagctgaa gggcatcgac ttcaaggagg acggcaacat cctggggcac | | 420 |
| aagctggagt acaactacaa cagccacaac gtctatatca tggccgacaa gcagaagaac | | 480 |
| ggcatcaagg tgaacttcaa gatccgccac aacatcgagg acggcagcgt gcagctcgcc | | 540 |
| gaccactacc agcagaacac ccccatcggc gacggccccg tgctgctgcc cgacaaccac | | 600 |
| tacctgagca cccagtccgc cctgagcaaa gaccccaacg agaagcgcga tcacatggtc | | 660 |
| ctgctggagt tcgtgaccgc cgccgggatc actctcggca tggacgagct gtacaagta | | 719 |

<210> SEQ ID NO 4
<211> LENGTH: 21
<212> TYPE: DNA
<213> ORGANISM: Artificial sequence
<220> FEATURE:
<223> OTHER INFORMATION: external primer

<400> SEQUENCE: 4

| | |
|---|---|
| taggtagggg atcgggactc t | 21 |

<210> SEQ ID NO 5
<211> LENGTH: 21
<212> TYPE: DNA
<213> ORGANISM: Artificial sequence
<220> FEATURE:
<223> OTHER INFORMATION: external primer

<400> SEQUENCE: 5

| | |
|---|---|
| gcgaagagtt tgtcctcaac c | 21 |

<210> SEQ ID NO 6
<211> LENGTH: 21
<212> TYPE: DNA
<213> ORGANISM: Artificial sequence
<220> FEATURE:

-continued

```
<223> OTHER INFORMATION: internal primer

<400> SEQUENCE: 6
cccatcaagc tgatccggaa c                                      21

<210> SEQ ID NO 7
<211> LENGTH: 21
<212> TYPE: DNA
<213> ORGANISM: Artificial sequence
<220> FEATURE:
<223> OTHER INFORMATION: internal primer

<400> SEQUENCE: 7
gtgaacagct cctcgccctt g                                      21
```